US009486467B2

(12) United States Patent
Rosin-Arbesfeld

(10) Patent No.: US 9,486,467 B2
(45) Date of Patent: Nov. 8, 2016

(54) METHOD OF TREATING COLORECTAL CANCER THAT EXPRESSES A MUTATED APC GENE BY ADMINISTERING ERYTHROMYCIN OR TYLOSIN

(75) Inventor: Rina Rosin-Arbesfeld, Herzlia (IL)

(73) Assignee: RAMOT AT TEL-AVIV UNIVERSITY LTD., Tel Aviv (IL)

(*) Notice: Subject to any disclaimer, the term of this patent is extended or adjusted under 35 U.S.C. 154(b) by 1196 days.

(21) Appl. No.: 12/308,452

(22) PCT Filed: Jun. 12, 2007

(86) PCT No.: PCT/IL2007/000706
§ 371 (c)(1),
(2), (4) Date: Apr. 7, 2010

(87) PCT Pub. No.: WO2007/144876
PCT Pub. Date: Dec. 21, 2007

(65) Prior Publication Data
US 2011/0306571 A1    Dec. 15, 2011

Related U.S. Application Data

(60) Provisional application No. 60/812,605, filed on Jun. 12, 2006.

(51) Int. Cl.
A61K 31/7048    (2006.01)
(52) U.S. Cl.
CPC ................................. A61K 31/7048 (2013.01)
(58) Field of Classification Search
CPC ........... A61K 31/7048; C07D 313/00; A01N 43/00; C07H 17/08
See application file for complete search history.

(56) References Cited

U.S. PATENT DOCUMENTS

| | | | |
|---|---|---|---|
| 4,064,143 A | 12/1977 | Nagel | |
| 4,092,473 A | 5/1978 | Okamoto et al. | |
| 4,124,755 A | 11/1978 | Bright | |
| 4,174,391 A | 11/1979 | Chapman et al. | |
| 4,205,163 A | 5/1980 | Mori et al. | |
| 4,268,665 A | 5/1981 | Sakakibara et al. | |
| 4,429,116 A | 1/1984 | Nagel | |
| 5,324,720 A | 6/1994 | Holt et al. | |
| 5,602,106 A | 2/1997 | Ajito et al. | |
| 5,872,103 A * | 2/1999 | Belletti | 514/26 |
| 6,127,415 A * | 10/2000 | Pfahl et al. | 514/543 |
| 6,777,543 B2 | 8/2004 | Wu et al. | |
| 6,825,171 B2 | 11/2004 | Wu | |
| 2003/0018049 A1 | 1/2003 | Godek et al. | |
| 2005/0171032 A1 | 8/2005 | Solomon | |

FOREIGN PATENT DOCUMENTS

| | | |
|---|---|---|
| CN | 1332746 A | 1/2002 |
| CN | 1562066 A | 1/2005 |
| WO | 00/40589 A2 | 7/2000 |
| WO | 02/50093 | 6/2002 |
| WO | 2006/016167 A2 | 2/2006 |

OTHER PUBLICATIONS

"Breast Cancer", Merck Manual Online Edition, [retrieved on Nov. 22, 2011]. Retrieved from the Internet http://www.merckmanuals.com/home. Revision Nov. 2008.*
Ries, et al., Cancer, 2000, vol. 88, No. 10, p. 2398-2424.*
Sassa, et al., Abstract ofInfectious Disease and Therapy (2000), 23(New Considerations for Macrolides, Azalides, Streptogramins, and Ketolides), 283-292. Retrieved from STN database on Nov. 23, 2011. 1 page.*
Sassa et al., Infectious Disease and Therapy, 2000, 23, 283-292.*
Steinbach et al., Ann. Intern Med., 1999, 131, 88-95.*
Fedwick et al, Infection and Immunity, 2005, 73(12), 7844-7852.*
Allen, L. V & Popovich, N. G. (2005). Ansel's pharmaceutical dosage forms and drug delivery systems. New York, NY: Lippincott Williams & Wilkins.*
Goldin, B. R & Gorbach, S. L. (1981). Effect of antibiotics on incidence of rat intestinal tumors induced by 1, 2-dimethylhydrazine dihydrochloride. Journal of the National Cancer Institute, 67(4), 877-880.*
Strle, F., Pleterski-Rigler, D., Cimperman, J., Pejovnik-Pustinek, A., Ruzic, E., & Stanek, G. (1992). Solitary borrelial lymphocytoma: report of 36 cases. Infection, 20(4), 201-206.*
"Prevention" in Glossary of medical education terms: Parts 1-7. Wojtczak, A., Ed. Medical Teacher. vol. 24, Nos. 2-6 and vol. 25, No. 1&2. 2002.*
Mizuno, S., Morita, Y., Inui, T., Asakawa, A., Ueno, N., Ando, T., . . . & Inui, A. (2005). Helicobacter pylori infection is associated with colon adenomatous polyps detected by high-resolution colonoscopy. International journal of cancer, 117(6), 1058-1059.*
Moertel, C. G. (1994). Chemotherapy for colorectal cancer. New England Journal of Medicine, 330(16), 1136-1142.*
Shilyansky, J., Lelli, J. L., Drongowski, R. A., & Coran, A. G. (1997). Efficacy of the straight endorectal pull-through in the management of familial adenomatous polyposis—a 16-year experience. Journal of pediatric surgery, 32(8), 1139-1143.*
Chen, S. Z., Jiang, M., & Zhen, Y. S. (2005). HERG K+ channel expression-related chemosensitivity in cancer cells and its modulation by erythromycin. Cancer chemotherapy and pharmacology, 56(2), 212-220.*
Smith, G., Carey, F. A., Beattie, J., Wilkie, M. J., Lightfoot, T. J., Coxhead, J., . . . & Wolf, C. R. (2002). Mutations in APC, Kirsten-ras, and p53—alternative genetic pathways to colorectal cancer. Proceedings of the National Academy of Sciences, 99(14), 9433-9438.*

(Continued)

Primary Examiner — Eric Olson
Assistant Examiner — Dale R Miller
(74) Attorney, Agent, or Firm — Browdy and Neimark, PLLC

(57) ABSTRACT

The present invention includes methods for treating or preventing a cancer in a mammal comprising administering to the mammal a therapeutically effective amount of a macrolide antibiotic such as tylosin, erythromycin, oleandomycin, spiramycin, and pharmaceutically acceptable salts and derivatives thereof.

14 Claims, 5 Drawing Sheets

(56) References Cited

OTHER PUBLICATIONS

Bedwell, D.M. et al.; Suppression of a CFTR premature stop mutation in a bronchial epithelial cell line. Nat. Med., 1997, 3:1280-1284.

Wilschanski, M., et al.; Gentamicin-induced correction of CFTR function in patients with cystic fibrosis and CFTR stop mutations. N. Engl. J. Med., 2003, 15:1433-1441.

Barton-Davis, E.R. et al.; Aminoglycoside antibiotics restore dystrophin function to skeletal muscles of mdx mice. J. Clin. Invest., 1999, 104:375-38.

Politano, L., et al.; Gentamicin administration in Duchenne patients with premature stop codon: Preliminary results. Acta Myol., 2003 1:15-21.

Kerem, E.; Pharmacologic therapy for stop mutations: how much CFTR activity is enough? Curr. Opin. Pulm. Med. 2004, 6:547-52.

Laurent-Puig, et al.; APC gene: database of germline and somatic mutations in human tumors and cell lines. Nucleic Acids Research, 1998, 26:269-270.

Thompson, J., et al.; Effects of a number of classes of 50S inhibitors on stop codon readthrough during protein synthesis. Antimicrob. Agents Chemother. 2004, 12:4889-4891.

Atkinson, J.; et al.; Mutations to nonsense codons in human genetic disease: implications for gene therapy by nonsense suppressor tRNAs. Nucleic Acids Res., 1994, 8:1327-1334.

Alman, B.A., et al.; Increased beta-catenin protein and somatic APC mutations in sporadic aggressive fibromatoses (desmoid tumors). Am. J. Pathol. 1997, 151:329-334.

Bohm, M., et al.; Deletion analysis at the DEL-27, APC and MTS1 loci in bladder cancer: LOH at the DEL-27 locus on 5p13-12 is a prognostic marker of tumor progression. Int. J. Cancer, 1997, 74:291-295.

Oh, S.T., et al.; Frequent somatic mutations for the beta-catenin gene in intestinal-type gastric cancer. Cancer Res., 1999, 59: 4257-4260.

Wills, J.C. et al.; "Hot spots" can burn you, Am. J. Gastroenterology, 2002, 97(3):757-758.

Fearnhead et al.; The ABC of APC. Hum. Mol. Genet., 2001, 10:721-723.

Crabtree et al.; Refining the Relation Between "First Hits" and "Second Hits" at the APC Locus: the "Loose Fit" Model and Evidence for Differences in Somatic Mutation Spectra Among Patients, Oncogene, 2003, 22:4257-4265.

Albuquerque et al., The "Just-Right" Signaling Model: APC Somatic Mutations are Selected Based on a Specific Level of Activation of the b-Catenin Signaling Cascade, Hum. Mol. Genet., 2002, 11:1549-1560.

Merck Index, 11th Edition, 1989, paragraph 8708.

Lightfoot et al; Treatment of Postoperative Ileus After Bowel Surgery With Low-dose Intravenous Erythromycin, Urology, 2007 69:611-615.

\* cited by examiner

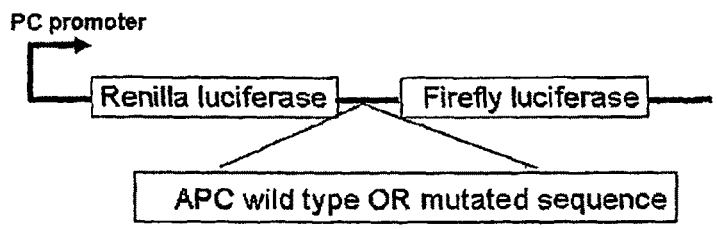
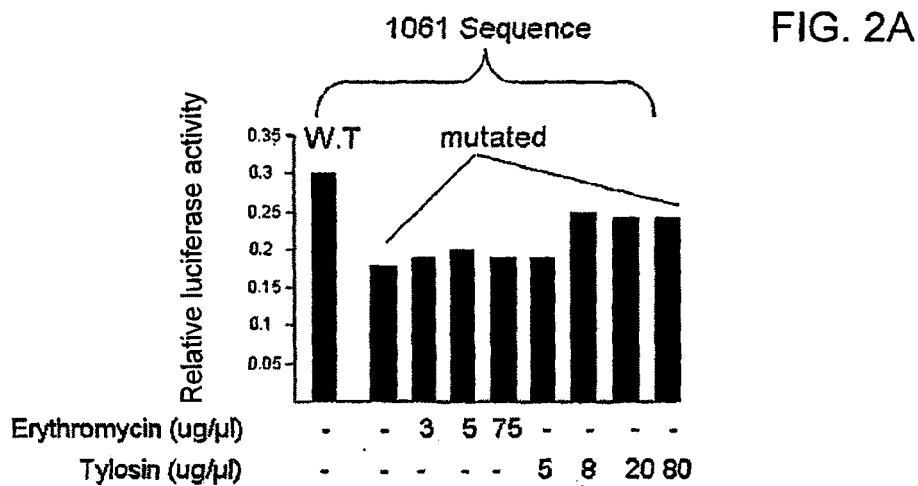
FIG. 2A
FIG. 2B
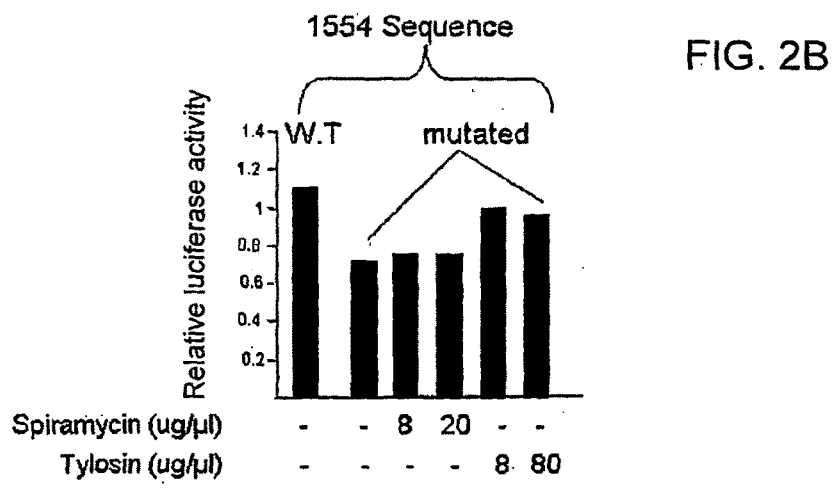
FIG. 2C

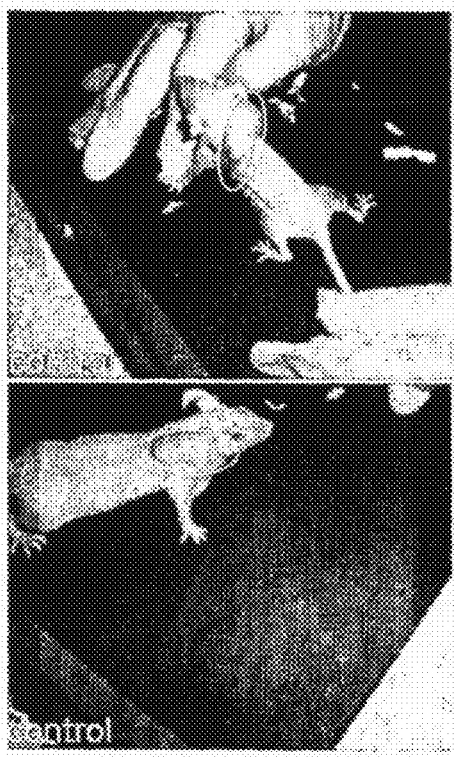
FIG. 4A
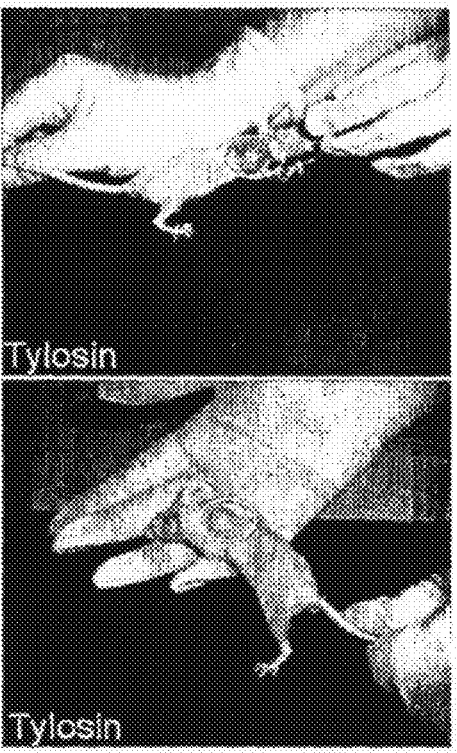
FIG. 4B
FIG. 4C
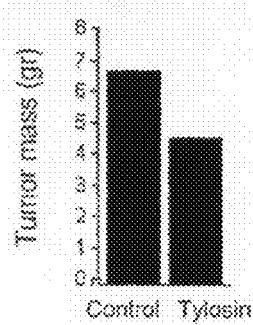
FIG. 4D
FIG. 4E

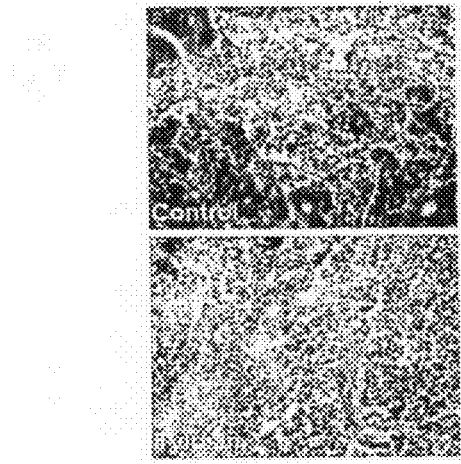
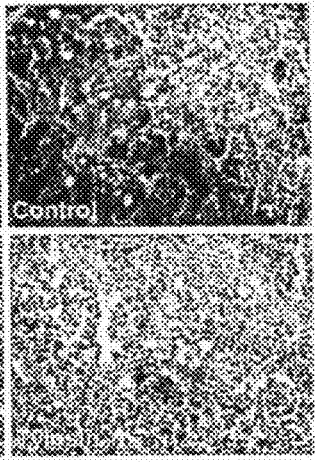
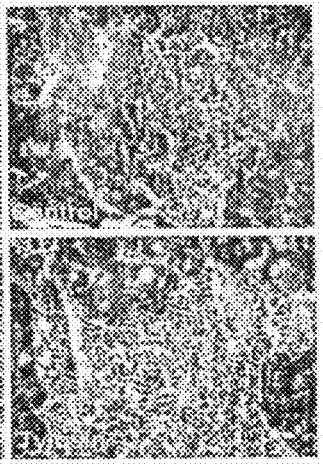
FIG. 5A   FIG. 5B   FIG. 5C
FIG. 5D   FIG. 5E   FIG. 5F
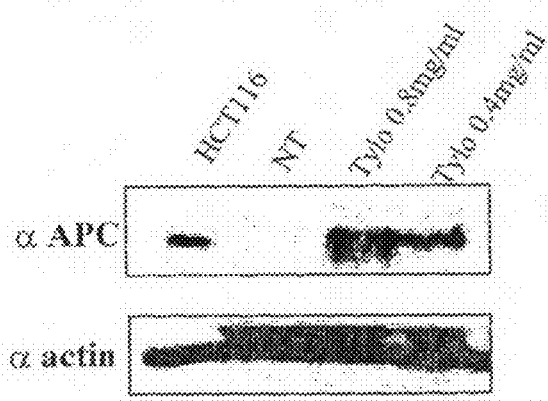
FIG. 6

SEQUENCE LISTING

```
<160> NUMBER OF SEQ ID NOS: 10

<210> SEQ ID NO 1
<211> LENGTH: 2843
<212> TYPE: PRT
<213> ORGANISM: Homo sapiens

<400> SEQUENCE: 1

Met Ala Ala Ala Ser Tyr Asp Gln Leu Leu Lys Gln Val Glu Ala Leu
1               5                   10                  15

Lys Met Glu Asn Ser Asn Leu Arg Gln Glu Leu Glu Asp Asn Ser Asn
            20                  25                  30
```

His Leu Thr Lys Leu Glu Thr Glu Ala Ser Asn Met Lys Glu Val Leu
             35                  40                  45

Lys Gln Leu Gln Gly Ser Ile Glu Asp Glu Ala Met Ala Ser Ser Gly
 50                  55                  60

Gln Ile Asp Leu Leu Glu Arg Leu Lys Glu Leu Asn Leu Asp Ser Ser
 65                  70                  75                  80

Asn Phe Pro Gly Val Lys Leu Arg Ser Lys Met Ser Leu Arg Ser Tyr
                 85                  90                  95

Gly Ser Arg Glu Gly Ser Val Ser Arg Ser Gly Glu Cys Ser Pro
                100                 105                 110

Val Pro Met Gly Ser Phe Pro Arg Arg Gly Phe Val Asn Gly Ser Arg
             115                 120                 125

Glu Ser Thr Gly Tyr Leu Glu Glu Leu Glu Lys Glu Arg Ser Leu Leu
             130                 135                 140

Leu Ala Asp Leu Asp Lys Glu Glu Lys Glu Lys Asp Trp Tyr Tyr Ala
145                 150                 155                 160

Gln Leu Gln Asn Leu Thr Lys Arg Ile Asp Ser Leu Pro Leu Thr Glu
                165                 170                 175

Asn Phe Ser Leu Gln Thr Asp Met Thr Arg Arg Gln Leu Glu Tyr Glu
             180                 185                 190

Ala Arg Gln Ile Arg Val Ala Met Glu Glu Gln Leu Gly Thr Cys Gln
             195                 200                 205

Asp Met Glu Lys Arg Ala Gln Arg Arg Ile Ala Arg Ile Gln Gln Ile
             210                 215                 220

Glu Lys Asp Ile Leu Arg Ile Arg Gln Leu Leu Gln Ser Gln Ala Thr
225                 230                 235                 240

Glu Ala Glu Arg Ser Ser Gln Asn Lys His Glu Thr Gly Ser His Asp
                245                 250                 255

Ala Glu Arg Gln Asn Glu Gly Gln Gly Val Gly Glu Ile Asn Met Ala
             260                 265                 270

Thr Ser Gly Asn Gly Gln Gly Ser Thr Thr Arg Met Asp His Glu Thr
             275                 280                 285

Ala Ser Val Leu Ser Ser Ser Thr His Ser Ala Pro Arg Arg Leu
             290                 295                 300

Thr Ser His Leu Gly Thr Lys Val Glu Met Val Tyr Ser Leu Leu Ser
305                 310                 315                 320

Met Leu Gly Thr His Asp Lys Asp Asp Met Ser Arg Thr Leu Leu Ala
                325                 330                 335

Met Ser Ser Ser Gln Asp Ser Cys Ile Ser Met Arg Gln Ser Gly Cys
             340                 345                 350

Leu Pro Leu Leu Ile Gln Leu Leu His Gly Asn Asp Lys Asp Ser Val
             355                 360                 365

Leu Leu Gly Asn Ser Arg Gly Ser Lys Glu Ala Arg Ala Arg Ala Ser
             370                 375                 380

Ala Ala Leu His Asn Ile Ile His Ser Gln Pro Asp Asp Lys Arg Gly
385                 390                 395                 400

Arg Arg Glu Ile Arg Val Leu His Leu Leu Glu Gln Ile Arg Ala Tyr
                405                 410                 415

Cys Glu Thr Cys Trp Glu Trp Gln Glu Ala His Glu Pro Gly Met Asp
             420                 425                 430

Gln Asp Lys Asn Pro Met Pro Ala Pro Val Glu His Gln Ile Cys Pro
             435                 440                 445

-continued

Ala Val Cys Val Leu Met Lys Leu Ser Phe Asp Glu Glu His Arg His
450                 455                 460

Ala Met Asn Glu Leu Gly Gly Leu Gln Ala Ile Ala Glu Leu Leu Gln
465                 470                 475                 480

Val Asp Cys Glu Met Tyr Gly Leu Thr Asn Asp His Tyr Ser Ile Thr
            485                 490                 495

Leu Arg Arg Tyr Ala Gly Met Ala Leu Thr Asn Leu Thr Phe Gly Asp
        500                 505                 510

Val Ala Asn Lys Ala Thr Leu Cys Ser Met Lys Gly Cys Met Arg Ala
            515                 520                 525

Leu Val Ala Gln Leu Lys Ser Glu Ser Glu Asp Leu Gln Gln Val Ile
530                 535                 540

Ala Ser Val Leu Arg Asn Leu Ser Trp Arg Ala Asp Val Asn Ser Lys
545                 550                 555                 560

Lys Thr Leu Arg Glu Val Gly Ser Val Lys Ala Leu Met Glu Cys Ala
                565                 570                 575

Leu Glu Val Lys Lys Glu Ser Thr Leu Lys Ser Val Leu Ser Ala Leu
            580                 585                 590

Trp Asn Leu Ser Ala His Cys Thr Glu Asn Lys Ala Asp Ile Cys Ala
        595                 600                 605

Val Asp Gly Ala Leu Ala Phe Leu Val Gly Thr Leu Thr Tyr Arg Ser
610                 615                 620

Gln Thr Asn Thr Leu Ala Ile Ile Glu Ser Gly Gly Ile Leu Arg
625                 630                 635                 640

Asn Val Ser Ser Leu Ile Ala Thr Asn Glu Asp His Arg Gln Ile Leu
                645                 650                 655

Arg Glu Asn Asn Cys Leu Gln Thr Leu Leu Gln His Leu Lys Ser His
            660                 665                 670

Ser Leu Thr Ile Val Ser Asn Ala Cys Gly Thr Leu Trp Asn Leu Ser
        675                 680                 685

Ala Arg Asn Pro Lys Asp Gln Glu Ala Leu Trp Asp Met Gly Ala Val
690                 695                 700

Ser Met Leu Lys Asn Leu Ile His Ser Lys His Lys Met Ile Ala Met
705                 710                 715                 720

Gly Ser Ala Ala Ala Leu Arg Asn Leu Met Ala Asn Arg Pro Ala Lys
                725                 730                 735

Tyr Lys Asp Ala Asn Ile Met Ser Pro Gly Ser Ser Leu Pro Ser Leu
            740                 745                 750

His Val Arg Lys Gln Lys Ala Leu Glu Ala Glu Leu Asp Ala Gln His
        755                 760                 765

Leu Ser Glu Thr Phe Asp Asn Ile Asp Asn Leu Ser Pro Lys Ala Ser
770                 775                 780

His Arg Ser Lys Gln Arg His Lys Gln Ser Leu Tyr Gly Asp Tyr Val
785                 790                 795                 800

Phe Asp Thr Asn Arg His Asp Asp Asn Arg Ser Asp Asn Phe Asn Thr
                805                 810                 815

Gly Asn Met Thr Val Leu Ser Pro Tyr Leu Asn Thr Thr Val Leu Pro
            820                 825                 830

Ser Ser Ser Ser Ser Arg Gly Ser Leu Asp Ser Ser Arg Ser Glu Lys
        835                 840                 845

Asp Arg Ser Leu Glu Arg Glu Arg Gly Ile Gly Leu Gly Asn Tyr His
850                 855                 860

-continued

```
Pro Ala Thr Glu Asn Pro Gly Thr Ser Ser Lys Arg Gly Leu Gln Ile
865                 870                 875                 880

Ser Thr Thr Ala Ala Gln Ile Ala Lys Val Met Glu Glu Val Ser Ala
                885                 890                 895

Ile His Thr Ser Gln Glu Asp Arg Ser Ser Gly Ser Thr Thr Glu Leu
            900                 905                 910

His Cys Val Thr Asp Glu Arg Asn Ala Leu Arg Arg Ser Ser Ala Ala
        915                 920                 925

His Thr His Ser Asn Thr Tyr Asn Phe Thr Lys Ser Glu Asn Ser Asn
    930                 935                 940

Arg Thr Cys Ser Met Pro Tyr Ala Lys Leu Glu Tyr Lys Arg Ser Ser
945                 950                 955                 960

Asn Asp Ser Leu Asn Ser Val Ser Ser Asp Gly Tyr Gly Lys Arg
                965                 970                 975

Gly Gln Met Lys Pro Ser Ile Glu Ser Tyr Ser Glu Asp Glu Ser
                980                 985                 990

Lys Phe Cys Ser Tyr Gly Gln Tyr Pro Ala Asp Leu Ala His Lys Ile
            995                1000                1005

His Ser Ala Asn His Met Asp Asp Asn Asp Gly Glu Leu Asp Thr
    1010                1015                1020

Pro Ile Asn Tyr Ser Leu Lys Tyr Ser Asp Glu Gln Leu Asn Ser
    1025                1030                1035

Gly Arg Gln Ser Pro Ser Gln Asn Glu Arg Trp Ala Arg Pro Lys
    1040                1045                1050

His Ile Ile Glu Asp Glu Ile Lys Gln Ser Glu Gln Arg Gln Ser
    1055                1060                1065

Arg Asn Gln Ser Thr Thr Tyr Pro Val Tyr Thr Glu Ser Thr Asp
    1070                1075                1080

Asp Lys His Leu Lys Phe Gln Pro His Phe Gly Gln Gln Glu Cys
    1085                1090                1095

Val Ser Pro Tyr Arg Ser Arg Gly Ala Asn Gly Ser Glu Thr Asn
    1100                1105                1110

Arg Val Gly Ser Asn His Gly Ile Asn Gln Asn Val Ser Gln Ser
    1115                1120                1125

Leu Cys Gln Glu Asp Asp Tyr Glu Asp Asp Lys Pro Thr Asn Tyr
    1130                1135                1140

Ser Glu Arg Tyr Ser Glu Glu Gln His Glu Glu Glu Arg
    1145                1150                1155

Pro Thr Asn Tyr Ser Ile Lys Tyr Asn Glu Glu Lys Arg His Val
    1160                1165                1170

Asp Gln Pro Ile Asp Tyr Ser Leu Lys Tyr Ala Thr Asp Ile Pro
    1175                1180                1185

Ser Ser Gln Lys Gln Ser Phe Ser Phe Ser Lys Ser Ser Ser Gly
    1190                1195                1200

Gln Ser Ser Lys Thr Glu His Met Ser Ser Ser Glu Asn Thr
    1205                1210                1215

Ser Thr Pro Ser Ser Asn Ala Lys Arg Gln Asn Gln Leu His Pro
    1220                1225                1230

Ser Ser Ala Gln Ser Arg Ser Gly Gln Pro Gln Lys Ala Ala Thr
    1235                1240                1245

Cys Lys Val Ser Ser Ile Asn Gln Glu Thr Ile Gln Thr Tyr Cys
    1250                1255                1260
```

```
Val Glu Asp Thr Pro Ile Cys Phe Ser Arg Cys Ser Ser Leu Ser
    1265                1270                1275

Ser Leu Ser Ser Ala Glu Asp Glu Ile Gly Cys Asn Gln Thr Thr
    1280                1285                1290

Gln Glu Ala Asp Ser Ala Asn Thr Leu Gln Ile Ala Glu Ile Lys
    1295                1300                1305

Glu Lys Ile Gly Thr Arg Ser Ala Glu Asp Pro Val Ser Glu Val
    1310                1315                1320

Pro Ala Val Ser Gln His Pro Arg Thr Lys Ser Ser Arg Leu Gln
    1325                1330                1335

Gly Ser Ser Leu Ser Ser Glu Ser Ala Arg His Lys Ala Val Glu
    1340                1345                1350

Phe Ser Ser Gly Ala Lys Ser Pro Ser Lys Ser Gly Ala Gln Thr
    1355                1360                1365

Pro Lys Ser Pro Pro Glu His Tyr Val Gln Glu Thr Pro Leu Met
    1370                1375                1380

Phe Ser Arg Cys Thr Ser Val Ser Ser Leu Asp Ser Phe Glu Ser
    1385                1390                1395

Arg Ser Ile Ala Ser Ser Val Gln Ser Glu Pro Cys Ser Gly Met
    1400                1405                1410

Val Ser Gly Ile Ile Ser Pro Ser Asp Leu Pro Asp Ser Pro Gly
    1415                1420                1425

Gln Thr Met Pro Pro Ser Arg Ser Lys Thr Pro Pro Pro Pro Pro
    1430                1435                1440

Gln Thr Ala Gln Thr Lys Arg Glu Val Pro Lys Asn Lys Ala Pro
    1445                1450                1455

Thr Ala Glu Lys Arg Glu Ser Gly Pro Lys Gln Ala Ala Val Asn
    1460                1465                1470

Ala Ala Val Gln Arg Val Gln Val Leu Pro Asp Ala Asp Thr Leu
    1475                1480                1485

Leu His Phe Ala Thr Glu Ser Thr Pro Asp Gly Phe Ser Cys Ser
    1490                1495                1500

Ser Ser Leu Ser Ala Leu Ser Leu Asp Glu Pro Phe Ile Gln Lys
    1505                1510                1515

Asp Val Glu Leu Arg Ile Met Pro Pro Val Gln Glu Asn Asp Asn
    1520                1525                1530

Gly Asn Glu Thr Glu Ser Glu Gln Pro Lys Glu Ser Asn Glu Asn
    1535                1540                1545

Gln Glu Lys Glu Ala Glu Lys Thr Ile Asp Ser Glu Lys Asp Leu
    1550                1555                1560

Leu Asp Asp Ser Asp Asp Asp Asp Ile Glu Ile Leu Glu Glu Cys
    1565                1570                1575

Ile Ile Ser Ala Met Pro Thr Lys Ser Ser Arg Lys Ala Lys Lys
    1580                1585                1590

Pro Ala Gln Thr Ala Ser Lys Leu Pro Pro Pro Val Ala Arg Lys
    1595                1600                1605

Pro Ser Gln Leu Pro Val Tyr Lys Leu Leu Pro Ser Gln Asn Arg
    1610                1615                1620

Leu Gln Pro Gln Lys His Val Ser Phe Thr Pro Gly Asp Asp Met
    1625                1630                1635

Pro Arg Val Tyr Cys Val Glu Gly Thr Pro Ile Asn Phe Ser Thr
    1640                1645                1650
```

```
-continued

Ala Thr Ser Leu Ser Asp Leu Thr Ile Glu Ser Pro Pro Asn Glu
    1655                1660                1665

Leu Ala Ala Gly Glu Gly Val Arg Gly Gly Ala Gln Ser Gly Glu
    1670                1675                1680

Phe Glu Lys Arg Asp Thr Ile Pro Thr Glu Gly Arg Ser Thr Asp
    1685                1690                1695

Glu Ala Gln Gly Gly Lys Thr Ser Ser Val Thr Ile Pro Glu Leu
    1700                1705                1710

Asp Asp Asn Lys Ala Glu Glu Gly Asp Ile Leu Ala Glu Cys Ile
    1715                1720                1725

Asn Ser Ala Met Pro Lys Gly Lys Ser His Lys Pro Phe Arg Val
    1730                1735                1740

Lys Lys Ile Met Asp Gln Val Gln Gln Ala Ser Ala Ser Ser Ser
    1745                1750                1755

Ala Pro Asn Lys Asn Gln Leu Asp Gly Lys Lys Lys Lys Pro Thr
    1760                1765                1770

Ser Pro Val Lys Pro Ile Pro Gln Asn Thr Glu Tyr Arg Thr Arg
    1775                1780                1785

Val Arg Lys Asn Ala Asp Ser Lys Asn Asn Leu Asn Ala Glu Arg
    1790                1795                1800

Val Phe Ser Asp Asn Lys Asp Ser Lys Lys Gln Asn Leu Lys Asn
    1805                1810                1815

Asn Ser Lys Val Phe Asn Asp Lys Leu Pro Asn Asn Glu Asp Arg
    1820                1825                1830

Val Arg Gly Ser Phe Ala Phe Asp Ser Pro His His Tyr Thr Pro
    1835                1840                1845

Ile Glu Gly Thr Pro Tyr Cys Phe Ser Arg Asn Asp Ser Leu Ser
    1850                1855                1860

Ser Leu Asp Phe Asp Asp Asp Val Asp Leu Ser Arg Glu Lys
    1865                1870                1875

Ala Glu Leu Arg Lys Ala Lys Glu Asn Lys Glu Ser Glu Ala Lys
    1880                1885                1890

Val Thr Ser His Thr Glu Leu Thr Ser Asn Gln Gln Ser Ala Asn
    1895                1900                1905

Lys Thr Gln Ala Ile Ala Lys Gln Pro Ile Asn Arg Gly Gln Pro
    1910                1915                1920

Lys Pro Ile Leu Gln Lys Gln Ser Thr Phe Pro Gln Ser Ser Lys
    1925                1930                1935

Asp Ile Pro Asp Arg Gly Ala Ala Thr Asp Glu Lys Leu Gln Asn
    1940                1945                1950

Phe Ala Ile Glu Asn Thr Pro Val Cys Phe Ser His Asn Ser Ser
    1955                1960                1965

Leu Ser Ser Leu Ser Asp Ile Asp Gln Glu Asn Asn Lys Glu
    1970                1975                1980

Asn Glu Pro Ile Lys Glu Thr Glu Pro Pro Asp Ser Gln Gly Glu
    1985                1990                1995

Pro Ser Lys Pro Gln Ala Ser Gly Tyr Ala Pro Lys Ser Phe His
    2000                2005                2010

Val Glu Asp Thr Pro Val Cys Phe Ser Arg Asn Ser Ser Leu Ser
    2015                2020                2025

Ser Leu Ser Ile Asp Ser Glu Asp Asp Leu Leu Gln Glu Cys Ile
    2030                2035                2040
```

-continued

| | | | | | | | | | | | |
|---|---|---|---|---|---|---|---|---|---|---|---|
| Ser | Ser | Ala | Met | Pro | Lys | Lys | Lys | Pro | Ser | Arg | Leu | Lys | Gly |
| 2045 | | | | 2050 | | | | 2055 | | | |

Ser Ser Ala Met Pro Lys Lys Lys Pro Ser Arg Leu Lys Gly
 2045                2050               2055

Asp Asn Glu Lys His Ser Pro Arg Asn Met Gly Gly Ile Leu Gly
 2060                2065               2070

Glu Asp Leu Thr Leu Asp Leu Lys Asp Ile Gln Arg Pro Asp Ser
 2075                2080               2085

Glu His Gly Leu Ser Pro Asp Ser Glu Asn Phe Asp Trp Lys Ala
 2090                2095               2100

Ile Gln Glu Gly Ala Asn Ser Ile Val Ser Ser Leu His Gln Ala
 2105                2110               2115

Ala Ala Ala Ala Cys Leu Ser Arg Gln Ala Ser Ser Asp Ser Asp
 2120                2125               2130

Ser Ile Leu Ser Leu Lys Ser Gly Ile Ser Leu Gly Ser Pro Phe
 2135                2140               2145

His Leu Thr Pro Asp Gln Glu Glu Lys Pro Phe Thr Ser Asn Lys
 2150                2155               2160

Gly Pro Arg Ile Leu Lys Pro Gly Glu Lys Ser Thr Leu Glu Thr
 2165                2170               2175

Lys Lys Ile Glu Ser Glu Ser Lys Gly Ile Lys Gly Gly Lys Lys
 2180                2185               2190

Val Tyr Lys Ser Leu Ile Thr Gly Lys Val Arg Ser Asn Ser Glu
 2195                2200               2205

Ile Ser Gly Gln Met Lys Gln Pro Leu Gln Ala Asn Met Pro Ser
 2210                2215               2220

Ile Ser Arg Gly Arg Thr Met Ile His Ile Pro Gly Val Arg Asn
 2225                2230               2235

Ser Ser Ser Ser Thr Ser Pro Val Ser Lys Lys Gly Pro Pro Leu
 2240                2245               2250

Lys Thr Pro Ala Ser Lys Ser Pro Ser Glu Gly Gln Thr Ala Thr
 2255                2260               2265

Thr Ser Pro Arg Gly Ala Lys Pro Ser Val Lys Ser Glu Leu Ser
 2270                2275               2280

Pro Val Ala Arg Gln Thr Ser Gln Ile Gly Gly Ser Ser Lys Ala
 2285                2290               2295

Pro Ser Arg Ser Gly Ser Arg Asp Ser Thr Pro Ser Arg Pro Ala
 2300                2305               2310

Gln Gln Pro Leu Ser Arg Pro Ile Gln Ser Pro Gly Arg Asn Ser
 2315                2320               2325

Ile Ser Pro Gly Arg Asn Gly Ile Ser Pro Pro Asn Lys Leu Ser
 2330                2335               2340

Gln Leu Pro Arg Thr Ser Ser Pro Ser Thr Ala Ser Thr Lys Ser
 2345                2350               2355

Ser Gly Ser Gly Lys Met Ser Tyr Thr Ser Pro Gly Arg Gln Met
 2360                2365               2370

Ser Gln Gln Asn Leu Thr Lys Gln Thr Gly Leu Ser Lys Asn Ala
 2375                2380               2385

Ser Ser Ile Pro Arg Ser Glu Ser Ala Ser Lys Gly Leu Asn Gln
 2390                2395               2400

Met Asn Asn Gly Asn Gly Ala Asn Lys Lys Val Glu Leu Ser Arg
 2405                2410               2415

Met Ser Ser Thr Lys Ser Ser Gly Ser Glu Ser Asp Arg Ser Glu
 2420                2425               2430

```
Arg Pro Val Leu Val Arg Gln Ser Thr Phe Ile Lys Glu Ala Pro
2435                2440                2445

Ser Pro Thr Leu Arg Arg Lys Leu Glu Glu Ser Ala Ser Phe Glu
2450                2455                2460

Ser Leu Ser Pro Ser Ser Arg Pro Ala Ser Pro Thr Arg Ser Gln
2465                2470                2475

Ala Gln Thr Pro Val Leu Ser Pro Ser Leu Pro Asp Met Ser Leu
2480                2485                2490

Ser Thr His Ser Ser Val Gln Ala Gly Gly Trp Arg Lys Leu Pro
2495                2500                2505

Pro Asn Leu Ser Pro Thr Ile Glu Tyr Asn Asp Gly Arg Pro Ala
2510                2515                2520

Lys Arg His Asp Ile Ala Arg Ser His Ser Glu Ser Pro Ser Arg
2525                2530                2535

Leu Pro Ile Asn Arg Ser Gly Thr Trp Lys Arg Glu His Ser Lys
2540                2545                2550

His Ser Ser Ser Leu Pro Arg Val Ser Thr Trp Arg Arg Thr Gly
2555                2560                2565

Ser Ser Ser Ser Ile Leu Ser Ala Ser Ser Glu Ser Ser Glu Lys
2570                2575                2580

Ala Lys Ser Glu Asp Glu Lys His Val Asn Ser Ile Ser Gly Thr
2585                2590                2595

Lys Gln Ser Lys Glu Asn Gln Val Ser Ala Lys Gly Thr Trp Arg
2600                2605                2610

Lys Ile Lys Glu Asn Glu Phe Ser Pro Thr Asn Ser Thr Ser Gln
2615                2620                2625

Thr Val Ser Ser Gly Ala Thr Asn Gly Ala Glu Ser Lys Thr Leu
2630                2635                2640

Ile Tyr Gln Met Ala Pro Ala Val Ser Lys Thr Glu Asp Val Trp
2645                2650                2655

Val Arg Ile Glu Asp Cys Pro Ile Asn Asn Pro Arg Ser Gly Arg
2660                2665                2670

Ser Pro Thr Gly Asn Thr Pro Pro Val Ile Asp Ser Val Ser Glu
2675                2680                2685

Lys Ala Asn Pro Asn Ile Lys Asp Ser Lys Asp Asn Gln Ala Lys
2690                2695                2700

Gln Asn Val Gly Asn Gly Ser Val Pro Met Arg Thr Val Gly Leu
2705                2710                2715

Glu Asn Arg Leu Asn Ser Phe Ile Gln Val Asp Ala Pro Asp Gln
2720                2725                2730

Lys Gly Thr Glu Ile Lys Pro Gly Gln Asn Asn Pro Val Pro Val
2735                2740                2745

Ser Glu Thr Asn Glu Ser Ser Ile Val Glu Arg Thr Pro Phe Ser
2750                2755                2760

Ser Ser Ser Ser Ser Lys His Ser Ser Pro Ser Gly Thr Val Ala
2765                2770                2775

Ala Arg Val Thr Pro Phe Asn Tyr Asn Pro Ser Pro Arg Lys Ser
2780                2785                2790

Ser Ala Asp Ser Thr Ser Ala Arg Pro Ser Gln Ile Pro Thr Pro
2795                2800                2805

Val Asn Asn Asn Thr Lys Lys Arg Asp Ser Lys Thr Asp Ser Thr
2810                2815                2820
```

| | |
|---|---|
| Glu Ser Ser Gly Thr Gln Ser Pro Lys Arg His Ser Gly Ser Tyr | |
| 2825 2830 2835 | |
| Leu Val Thr Ser Val | |
| 2840 | |

<210> SEQ ID NO 2
<211> LENGTH: 8583
<212> TYPE: DNA
<213> ORGANISM: Homo sapiens

<400> SEQUENCE: 2

| | | | | |
|---|---|---|---|---|
| atggctgcag | cttcatatga | tcagttgtta | aagcaagttg | aggcactgaa gatggagaac | 60 |
| tcaaatcttc | gacaagagct | agaagataat | tccaatcatc | ttacaaaact ggaaactgag | 120 |
| gcatctaata | tgaaggaagt | acttaaacaa | ctacaaggaa | gtattgaaga tgaagctatg | 180 |
| gcttcttctg | gacagattga | tttattagag | cgtcttaaag | agcttaactt agatagcagt | 240 |
| aatttccctg | gagtaaaact | gcggtcaaaa | atgtccctcc | gttcttatgg aagccgggaa | 300 |
| ggatctgtat | caagccgttc | tggagagtgc | agtcctgttc | ctatgggttc atttccaaga | 360 |
| agagggtttg | taaatggaag | cagagaaagt | actggatatt | tagaagaact tgagaaagag | 420 |
| aggtcattgc | ttcttgctga | tcttgacaaa | gaagaaaagg | aaaaagactg gtattacgct | 480 |
| caacttcaga | atctcactaa | aagaatagat | agtcttcctt | taactgaaaa ttttttcctta | 540 |
| caaacagata | tgaccagaag | gcaattggaa | tatgaagcaa | ggcaaatcag agttgcgatg | 600 |
| gaagaacaac | taggtacctg | ccaggatatg | gaaaaacgag | cacagcgaag aatagccaga | 660 |
| attcagcaaa | tcgaaaagga | catacttcgt | atacgcagc | ttttacagtc ccaagcaaca | 720 |
| gaagcagaga | ggtcatctca | gaacaagcat | gaaaccggct | cacatgatgc tgagcggcag | 780 |
| aatgaaggtc | aaggagtggg | agaaatcaac | atggcaactt | ctggtaatgg tcagggttca | 840 |
| actacacgaa | tggaccatga | aacagccagt | gttttgagtt | ctagtagcac acactctgca | 900 |
| cctcgaaggc | tgacaagtca | tctgggaacc | aaggtggaaa | tggtgtattc attgttgtca | 960 |
| atgcttggta | ctcatgataa | ggatgatatg | tcgcgaactt | tgctagctat gtctagctcc | 1020 |
| caagacagct | gtatatccat | gcgacagtct | ggatgtcttc | ctctcctcat ccagcttttta | 1080 |
| catggcaatg | acaaagactc | tgtattgttg | ggaaattccc | ggggcagtaa agaggctcgg | 1140 |
| gccagggcca | gtcagcact | ccacaacatc | attcactcac | agcctgatga caagagaggc | 1200 |
| aggcgtgaaa | tccgagtcct | tcatcttttg | gaacagatac | gcgcttactg tgaaacctgt | 1260 |
| tgggagtggc | aggaagctca | tgaaccaggc | atggaccagg | acaaaaatcc aatgccagct | 1320 |
| cctgttgaac | atcagatctg | tcctgctgtg | tgtgttctaa | tgaaactttc atttgatgaa | 1380 |
| gagcatagac | atgcaatgaa | tgaactaggg | gactacagg | ccattgcaga attattgcaa | 1440 |
| gtggactgtg | aaatgtatgg | gcttactaat | gaccactaca | gtattacact aagacgatat | 1500 |
| gctggaatgg | ctttgacaaa | cttgacttttt | ggagatgtag | ccaacaaggc tacgctatgc | 1560 |
| tctatgaaag | gctgcatgag | agcacttgtg | gcccaactaa | atctgaaag tgaagactta | 1620 |
| cagcaggtta | ttgcgagtgt | tttgaggaat | ttgtcttggc | gagcagatgt aaatagtaaa | 1680 |
| aagacgttgc | gagaagttgg | aagtgtgaaa | gcattgatgg | aatgtgcttt agaagttaaa | 1740 |
| aaggaatcaa | ccctcaaaag | cgtattgagt | gccttatgga | atttgtcagc acattgcact | 1800 |
| gagaataaag | ctgatatatg | tgctgtagat | ggtgcacttg | cattttttggt tggcactctt | 1860 |
| acttaccgga | gccagacaaa | cactttagcc | attattgaaa | gtggaggtgg gatattacgg | 1920 |
| aatgtgtcca | gcttgatagc | tacaaatgag | gaccacaggc | aaatcctaag agagaacaac | 1980 |

```
tgtctacaaa ctttattaca acacttaaaa tctcatagtt tgacaatagt cagtaatgca    2040
tgtggaactt tgtggaatct ctcagcaaga aatcctaaag accaggaagc attatgggac    2100
atgggggcag ttagcatgct caagaacctc attcattcaa agcacaaaat gattgctatg    2160
ggaagtgctg cagctttaag gaatctcatg gcaaataggc ctgcgaagta caaggatgcc    2220
aatattatgt ctcctggctc aagcttgcca tctcttcatg ttaggaaaca aaaagcccta    2280
gaagcagaat tagatgctca gcacttatca gaacttttg acaatataga caatttaagt    2340
cccaaggcat ctcatcgtag taagcagaga cacaagcaaa gtctctatgg tgattatgtt    2400
tttgacacca atcgacatga tgataatagg tcagacaatt ttaatactgg caacatgact    2460
gtcctttcac catatttgaa tactacagtg ttacccagct cctcttcatc aagaggaagc    2520
ttagatagtt ctcgttctga aaagataga agtttggaga gagaacgcgg aattggtcta    2580
ggcaactacc atccagcaac agaaaatcca ggaacttctt caaagcgagg tttgcagatc    2640
tccaccactg cagcccagat tgccaaagtc atggaagaag tgtcagccat tcatacctct    2700
caggaagaca gaagttctgg gtctaccact gaattacatt gtgtgacaga tgagagaaat    2760
gcacttagaa gaagctctgc tgcccataca cattcaaaca cttacaattt cactaagtcg    2820
gaaaattcaa ataggacatg ttctatgcct tatgccaaat tagaatacaa gagatcttca    2880
aatgatagtt taaatagtgt cagtagtagt gatggttatg gtaaaagagg tcaaatgaaa    2940
ccctcgattg aatcctattc tgaagatgat gaaagtaagt tttgcagtta tggtcaatac    3000
ccagccgacc tagcccataa aatacatagt gcaaatcata tggatgataa tgatggagaa    3060
ctagatacac aataaaatta tagtcttaaa tattcagatg agcagttgaa ctctggaagg    3120
caaagtcctt cacagaatga agatgggca agacccaaac acataataga agatgaaata    3180
aaacaaagtg agcaaagaca atcaaggaat caaagtacaa cttatcctgt ttatactgag    3240
agcactgatg ataaacacct caagttccaa ccacattttg gacagcagga atgtgtttct    3300
ccatacaggt cacggggagc caatggttca gaaacaaatc gagtgggttc taatcatgga    3360
attaatcaaa atgtaagcca gtctttgtgt caagaagatg actatgaaga tgataagcct    3420
accaattata gtgaacgtta ctctgaagaa gaacagcatg aagaagaaga gagaccaaca    3480
aattatagca taaaatataa tgaagagaaa cgtcatgtgg atcagcctat tgattatagt    3540
ttaaaatatg ccacagatat tccttcatca cagaaacagt cattttcatt ctcaaagagt    3600
tcatctggac aaagcagtaa aaccgaacat atgtcttcaa gcagtgagaa tacgtccaca    3660
ccttcatcta tgccaagag gcagaatcag ctccatccaa gttctgcaca gagtagaagt    3720
ggtcagcctc aaaaggctgc cacttgcaaa gtttcttcta ttaaccaaga aacaatacag    3780
acttattgtg tagaagatac tccaatatgt tttcaagat gtagttcatt atcatctttg    3840
tcatcagctg aagatgaaat aggatgtaat cagacgacac aggaagcaga ttctgctaat    3900
accctgcaaa tagcagaaat aaaagaaaag attggaacta ggtcagctga agatcctgtg    3960
agcgaagttc cagcagtgtc acagcaccct agaaccaaat ccagcagact gcagggttct    4020
agtttatctt cagaatcagc caggcacaaa gctgttgaat tttcttcagg agcgaaatct    4080
ccctccaaaa gtggtgctca gacacccaaa agtccacctg aacactatgt tcaggagacc    4140
ccactcatgt ttagcagatg tacttctgtc agttcacttg atagttttga gagtcgttcg    4200
attgccagct ccgttcagag tgaaccatgc agtggaatgg taagtggcat tataagcccc    4260
agtgatcttc cagatagccc tggacaaacc atgccaccaa gcagaagtaa acacctcca    4320 ccacctcctc aaacagctca aaccaagcga gaagtaccta aaaataaagc acctactgct    4380
```

-continued

| | | | | | |
|---|---|---|---|---|---|
| gaaaagagag | agagtggacc | taagcaagct | gcagtaaatg | ctgcagttca | gagggtccag | 4440 |
| gttcttccag | atgctgatac | tttattacat | tttgccacgg | aaagtactcc | agatggattt | 4500 |
| tcttgttcat | ccagcctgag | tgctctgagc | ctcgatgagc | catttataca | gaaagatgtg | 4560 |
| gaattaagaa | taatgcctcc | agttcaggaa | atgacaatg | ggaatgaaac | agaatcagag | 4620 |
| cagcctaaag | aatcaaatga | aaaccaagag | aaagaggcag | aaaaaactat | tgattctgaa | 4680 |
| aaggacctat | tagatgattc | agatgatgat | gatattgaaa | tactagaaga | atgtattatt | 4740 |
| tctgccatgc | caacaaagtc | atcacgtaaa | gcaaaaaagc | cagcccagac | tgcttcaaaa | 4800 |
| ttacctccac | ctgtggcaag | gaaaccaagt | cagctgcctg | tgtacaaact | tctaccatca | 4860 |
| caaaacaggt | tgcaaccccca | aaagcatgtt | agttttacac | cggggatga | tatgccacgg | 4920 |
| gtgtattgtg | ttgaagggac | acctataaac | ttttccacag | ctacatctct | aagtgatcta | 4980 |
| acaatcgaat | ccctccaaa | tgagttagct | gctggagaag | gagttagagg | aggggcacag | 5040 |
| tcaggtgaat | ttgaaaaacg | agataccatt | cctacagaag | gcagaagtac | agatgaggct | 5100 |
| caaggaggaa | aaacctcatc | tgtaaccata | cctgaattgg | atgacaataa | agcagaggaa | 5160 |
| ggtgatattc | ttgcagaatg | cattaattct | gctatgccca | aagggaaaag | tcacaagcct | 5220 |
| ttccgtgtga | aaaagataat | ggaccaggtc | cagcaagcat | ctgcgtcttc | ttctgcaccc | 5280 |
| aacaaaaatc | agttagatgg | taagaaaaag | aaaccaactt | caccagtaaa | acctatacca | 5340 |
| caaaatactg | aatataggac | acgtgtaaga | aaaaatgcag | actcaaaaaa | taatttaaat | 5400 |
| gctgagagag | ttttctcaga | caacaaagat | tcaagaaac | agaatttgaa | aaataattcc | 5460 |
| aaggtcttca | atgataagct | cccaaataat | gaagatagag | tcagaggaag | ttttgctttt | 5520 |
| gattcacctc | atcattacac | gcctattgaa | ggaactcctt | actgttttc | acgaaatgat | 5580 |
| tctttgagtt | ctctagattt | tgatgatgat | gatgttgacc | tttccaggga | aaaggctgaa | 5640 |
| ttaagaaagg | caaaagaaaa | taaggaatca | gaggctaaag | ttaccagcca | cacagaacta | 5700 |
| acctccaacc | aacaatcagc | taataagaca | caagctattg | caaagcagcc | aataaatcga | 5760 |
| ggtcagccta | aacccatact | tcagaaacaa | tccactttc | cccagtcatc | caaagacata | 5820 |
| ccagacagag | gggcagcaac | tgatgaaaag | ttacagaatt | ttgctattga | aaatactccg | 5880 |
| gtttgctttt | ctcataattc | ctctctgagt | tctctcagtg | acattgacca | agaaaacaac | 5940 |
| aataaagaaa | atgaacctat | caaagagact | gagcccctg | actcacaggg | agaaccaagt | 6000 |
| aaacctcaag | catcaggcta | tgctcctaaa | tcatttcatg | ttgaagatac | cccagtttgt | 6060 |
| ttctcaagaa | acagttctct | cagttctctt | agtattgact | ctgaagatga | cctgttgcag | 6120 |
| gaatgtataa | gctccgcaat | gccaaaaaag | aaaaagcctt | caagactcaa | gggtgataat | 6180 |
| gaaaacata | gtcccagaaa | tatgggtggc | atattaggtg | aagatctgac | acttgatttg | 6240 |
| aaagatatac | agagaccaga | ttcagaacat | ggtctatccc | ctgattcaga | aaattttgat | 6300 |
| tggaaagcta | ttcaggaagg | tgcaaattcc | atagtaagta | gtttacatca | agctgctgct | 6360 |
| gctgcatgtt | tatctagaca | agcttcgtct | gattcagatt | ccatcctttc | cctgaaatca | 6420 |
| ggaatctctc | tgggatcacc | atttcatctt | acacctgatc | aagaagaaaa | acccttaca | 6480 |
| agtaataaag | gcccacgaat | tctaaaacca | ggggagaaaa | gtacattgga | aactaaaaag | 6540 |
| atagaatctg | aaagtaaagg | aatcaaagga | ggaaaaaaag | tttataaaag | tttgattact | 6600 |
| ggaaaagttc | gatctaattc | agaaatttca | ggccaaatga | aacagcccct | tcaagcaaac | 6660 |
| atgccttcaa | tctctcgagg | caggacaatg | attcatattc | caggagttcg | aaatagctcc | 6720 |
| tcaagtacaa | gtcctgtttc | taaaaaaggc | ccaccccta | agactccagc | tccaaaagc | 6780 |

```
cctagtgaag gtcaaacagc caccacttct cctagaggag ccaagccatc tgtgaaatca    6840
gaattaagcc ctgttgccag gcagacatcc caaataggtg ggtcaagtaa agcaccttct    6900
agatcaggat ctagagattc gaccccttca agacctgccc agcaaccatt aagtagacct    6960
atacagtctc ctggccgaaa ctcaatttcc cctggtagaa atggaataag tcctcctaac    7020
aaattatctc aacttccaag gacatcatcc cctagtactg cttcaactaa gtcctcaggt    7080
tctggaaaaa tgtcatatac atctccaggt agacagatga ccaacagaa ccttaccaaa    7140
caaacaggtt tatccaagaa tgccagtagt attccaagaa gtgagtctgc ctccaaagga    7200
ctaaatcaga tgaataatgg taatggagcc aataaaaagg tagaactttc tagaatgtct    7260
tcaactaaat caagtggaag tgaatctgat agatcagaaa gacctgtatt agtacgccag    7320
tcaactttca tcaaagaagc tccaagccca accttaagaa gaaaattgga ggaatctgct    7380
tcatttgaat ctctttctcc atcatctaga ccagcttctc ccactaggtc ccaggcacaa    7440
actccagttt taagtccttc ccttcctgat atgtctctat ccacacattc gtctgttcag    7500
gctggtggat ggcgaaaact cccacctaat ctcagtccca ctatagagta taatgatgga    7560
agaccagcaa agcgccatga tattgcacgg tctcattctg aaagtccttc tagacttcca    7620
atcaataggt caggaacctg gaaacgtgag cacagcaaac attcatcatc ccttcctcga    7680
gtaagcactt ggagaagaac tggaagttca tcttcaattc tttctgcttc atcagaatcc    7740
agtgaaaaag caaaaagtga ggatgaaaaa catgtgaact ctatttcagg aaccaaacaa    7800
agtaaagaaa accaagtatc cgcaaaagga acatggagaa aaataaaaga aaatgaattt    7860
tctcccacaa atagtacttc tcagaccgtt tcctcaggtg ctacaaatgg tgctgaatca    7920
aagactctaa tttatcaaat ggcacctgct gtttctaaaa cagaggatgt ttgggtgaga    7980
attgaggact gtcccattaa caatcctaga tctggaagat ctcccacagg taatactccc    8040
ccggtgattg acagtgtttc agaaaaggca aatccaaaca ttaaagattc aaaagataat    8100
caggcaaaac aaaatgtggg taatggcagt gttcccatgc gtaccgtggg tttggaaaat    8160
cgcctgaact cctttattca ggtggatgcc cctgaccaaa aaggaactga gataaaacca    8220
ggacaaaata atcctgtccc tgtatcagag actaatgaaa gttctatagt ggaacgtacc    8280
ccattcagtt ctagcagctc aagcaaacac agttcaccta gtgggactgt tgctgccaga    8340
gtgactcctt ttaattacaa cccaagccct aggaaaagca gcgcagatag cacttcagct    8400
cggccatctc agatcccaac tccagtgaat aacaacacaa agaagcgaga ttccaaaact    8460
gacagcacag aatccagtgg aacccaaagt cctaagcgcc attctgggtc ttaccttgtg    8520
acatctgttt aaaagagagg aagaatgaaa ctaagaaaat tctatgttaa ttacaactgc    8580
tat                                                                  8583

<210> SEQ ID NO 3
<211> LENGTH: 21
<212> TYPE: DNA
<213> ORGANISM: Homo sapiens
<220> FEATURE:
<221> NAME/KEY: misc_feature
<222> LOCATION: (1)..(21)
<223> OTHER INFORMATION: wild-type sequence at site of codon 1061
      hotspot mutation

<400> SEQUENCE: 3
gaaataaaac aaagtgagca a                                               21
```

```
<210> SEQ ID NO 4
<211> LENGTH: 16
<212> TYPE: DNA
<213> ORGANISM: Homo sapiens
<220> FEATURE:
<221> NAME/KEY: misc_feature
<222> LOCATION: (1)..(16)
<223> OTHER INFORMATION: Mutated sequence
<220> FEATURE:
<221> NAME/KEY: misc_feature
<222> LOCATION: (10)..(12)
<223> OTHER INFORMATION: Frameshift stop codon

<400> SEQUENCE: 4
gaaataaagt gagcaa                                                     16

<210> SEQ ID NO 5
<211> LENGTH: 24
<212> TYPE: DNA
<213> ORGANISM: Homo sapiens
<220> FEATURE:
<221> NAME/KEY: misc_feature
<222> LOCATION: (1)..(24)
<223> OTHER INFORMATION: wild-type sequence at site of codon 1309
      hotspot mutations

<400> SEQUENCE: 5
ataaaagaaa agattggaac tagg                                            24

<210> SEQ ID NO 6
<211> LENGTH: 19
<212> TYPE: DNA
<213> ORGANISM: Homo sapiens
<220> FEATURE:
<221> NAME/KEY: misc_feature
<222> LOCATION: (1)..(19)
<223> OTHER INFORMATION: Mutated sequence
<220> FEATURE:
<221> NAME/KEY: misc_feature
<222> LOCATION: (16)..(18)
<223> OTHER INFORMATION: Frameshift stop codon

<400> SEQUENCE: 6
ataaaagatt ggaactagg                                                  19

<210> SEQ ID NO 7
<211> LENGTH: 15
<212> TYPE: DNA
<213> ORGANISM: Homo sapiens
<220> FEATURE:
<221> NAME/KEY: misc_feature
<222> LOCATION: (1)..(15)
<223> OTHER INFORMATION: wild-type sequence at site of codon 1450
      hotspot mutations

<400> SEQUENCE: 7
accaagcgag aagta                                                      15

<210> SEQ ID NO 8
<211> LENGTH: 15
<212> TYPE: DNA
<213> ORGANISM: Homo sapiens
<220> FEATURE:
<221> NAME/KEY: misc_feature
<222> LOCATION: (1)..(15)
<223> OTHER INFORMATION: Mutated sequence
<220> FEATURE:
<221> NAME/KEY: misc_feature
<222> LOCATION: (7)..(9)
<223> OTHER INFORMATION: Nonsence stop codon
```

```
<400> SEQUENCE: 8
accaagtgag aagta                                                    15

<210> SEQ ID NO 9
<211> LENGTH: 15
<212> TYPE: DNA
<213> ORGANISM: Homo sapiens
<220> FEATURE:
<221> NAME/KEY: misc_feature
<222> LOCATION: (1)..(15)
<223> OTHER INFORMATION: wild-type sequence at site of codon 1554
      hotspot mutations

<400> SEQUENCE: 9
gaaaaaacta ttgat                                                    15

<210> SEQ ID NO 10
<211> LENGTH: 16
<212> TYPE: DNA
<213> ORGANISM: Homo sapiens
<220> FEATURE:
<221> NAME/KEY: misc_feature
<222> LOCATION: (1)..(16)
<223> OTHER INFORMATION: Mutated sequence
<220> FEATURE:
<221> NAME/KEY: misc_feature
<222> LOCATION: (13)..(15)
<223> OTHER INFORMATION: Frameshift stop codon

<400> SEQUENCE: 10
gaaaaaaact attgat                                                   16
```

METHOD OF TREATING COLORECTAL CANCER THAT EXPRESSES A MUTATED APC GENE BY ADMINISTERING ERYTHROMYCIN OR TYLOSIN

CROSS-REFERENCE TO RELATED APPLICATIONS

The present application is a national phase entry under 35 USC §371 of International Application No.: PCT/IL2007/000706 filed Jun. 12, 2007, published in English, which claims benefit of U.S. Provisional Application Ser. No. 60/812,605, filed Jun. 12, 2006. The disclosures of all of said applications are incorporated herein by reference.

SEQUENCE LISTING

The instant application contains a sequence listing which has been submitted in ASCII format via EFS-Web and is hereby incorporated by reference in its entirety. Said ASCII copy, created on Jun. 10, 2007, is named 89-01.txt and is 37.9 kilobytes in size.

FIELD OF INVENTION

The invention relates to the treatment of cancers and more particularly to methods for treating colorectal cancer, Desmoid tumor, bladder cancer, gastric cancer, and breast cancer.

BACKGROUND OF THE INVENTION

Colorectal cancer (CRC) is a cancer of the large bowel and is the third most common cancer in men and women, representing 13% of all cancers. About 20% of patients have metastatic disease at the time of diagnosis, and 50% of all colorectal cancer patients will develop metastases and ultimately die from their disease. In the United States alone around 131,000 people will be diagnosed with colorectal cancer and 56,000 will die each year. The lifetime CRC risk in the general population is 5%, but this figure rises dramatically with age: by the age of 70 years, approximately half of the Western population will develop an adenoma. Nearly 85% of all CRC cases are sporadic in origin ("somatic CRC") and the rest occur as a result of an inherited genetic mutation ("hereditary CRC").

Colorectal cancers arise from adenomas, which are dysplastic but nonmalignant precursor lesions in the colon. Progression to carcinoma occurs through the accumulation of multiple somatic mutations, ultimately leading to malignant transformation and the formation of an invasive cancer. One of the most critical genes mutated in the progression to CRC is the Adenomatous Polyposis Coli (APC) tumor suppressor. Since APC mutations are detected very early in the adenoma-carcinoma sequence, the APC protein has been suggested to act as a gatekeeper of colorectal carcinogenesis, which means that functional loss of APC is very closely correlated with the future progression towards malignancy. Around 85% of all sporadic and hereditary colorectal tumors show loss of APC function. In addition to their role in hereditary and somatic CRC, mutations in APC have also been demonstrated in other cancer types, such as Desmoid tumor (aggressive fibromatoses) (11), bladder cancer (12), gastric cancer (13), and breast cancer (14).

APC is a large (312 kDa) protein that has many well-characterized functional domains and interacts with numerous other proteins. However, its critical role in tumorigenesis appears to lie in the control of cellular levels of β-catenin, thus acting as a negative regulator of the Wnt signaling pathway. When APC is mutated, the effector protein of the Wnt signaling pathway, β-catenin, accumulates and translocates into the nucleus. Once there it binds to the Tcf/LEF transcription factors and initiates transcription of a wide variety of genes. The downstream transcriptional activation targets of β-catenin include a number of genes involved in the development and progression of colorectal carcinoma, including Cyclin D1 and the oncogene c-myc. In addition to its role in the Wnt signaling pathway, loss of APC function results in disrupted cell-cell adhesion in cancer cells lacking APC.

Almost all (95%) APC mutations in CRC are nonsense or frameshift mutations that result in a truncated protein product with abnormal function. The sites of the APC mutations are usually not random; there are well-characterized hotspots for the APC-truncating mutations.

As in CRC, a large number of other human genetic diseases result from mutations that cause the premature termination of the synthesis of the protein encoded by the mutant gene, and one way of treating these diseases would be to supplement the mutant gene with a wild-type copy.

For some years it has been known that aminoglycoside antibiotics can suppress disease-associated premature stop mutations by allowing an amino acid to be incorporated in place of a stop codon, thus permitting translation to continue to the normal end of the transcript. Recent studies have shown that aminoglycosides can suppress premature stop mutations in mammalian transcripts both in vitro and in vivo to levels that restore physiologically relevant amounts of functional protein (1-5). The utility of this approach was previously demonstrated with the autosomal recessive disease cystic fibrosis (CF), and in Duchenne muscular dystrophy (DMD) patients with nonsense mutations. In both CF and DMD patients, only 5 to 10% of all cases are due to a nonsense mutation in the coding sequence. In comparison, in patients with colorectal tumors, premature stop codons in the APC gene are found in around 85% of all cases (6). However, studies aimed at restoring the full-length APC protein into cells that lack a functional APC protein have not been conducted so far.

Aminoglycosides such as gentamicin have serious dose-limiting toxicities and require intravenous administration, thus making them an unattractive long-term treatment for cancers.

The approach of suppressing stop codon mutations may be beneficial to other patients suffering from diseases that result from a stop codon mutation in an important gene (for example in patients suffering from APTR deficiency, antithromnin III, acid spingumyelias, and Hailey-Hailey disease, reviewed in (8)).

Recently, it has been shown that antibiotics of the macrolide family can target the ribosomal 50S subunit and induce stop codon readthrough in a prokaryotic system (7). U.S. Pat. No. 5,324,720 and U.S. Pat. Appl. Pub. No. 2005/0171032 relate to methods of treating cancer using certain macrolide antibiotics (9, 10).

SUMMARY OF THE INVENTION

The invention relates to the use of a macrolide antibiotic for the manufacture of a medicament for the treatment or prevention of a cancer selected from colorectal cancer, Desmoid tumor, bladder cancer, gastric cancer, and breast cancer, the macrolide antibiotic being one or more of:

tylosin, pharmaceutically acceptable salts thereof, and derivatives thereof;
erythromycin, pharmaceutically acceptable salts thereof, and derivatives thereof; oleandomycin, pharmaceutically acceptable salts thereof, and derivatives thereof; and spiramycin, pharmaceutically acceptable salts thereof and derivatives thereof.

The invention additionally relates to a pharmaceutical composition for the treatment or prevention of a cancer selected from colorectal cancer, Desmoid tumor, bladder cancer, gastric cancer, and breast cancer, comprising as an active ingredient a therapeutically effective amount of a macrolide antibiotic being one or more of:
tylosin, pharmaceutically acceptable salts thereof, and derivatives thereof;
erythromycin, pharmaceutically acceptable salts thereof, and derivatives thereof; oleandomycin, pharmaceutically acceptable salts thereof, and derivatives thereof; and spiramycin, pharmaceutically acceptable salts thereof, and derivatives thereof;
and a pharmaceutically acceptable carrier.

The invention further relates to the use of a macrolide antibiotic for the manufacture of a medicament for the treatment or prevention of a cancer that expresses a mutated APC (Adenomatous Polyposis Coli) gene, the macrolide antibiotic being one or more of:
tylosin, pharmaceutically acceptable salts thereof, and derivatives thereof;
erythromycin, pharmaceutically acceptable salts thereof, and derivatives thereof; oleandomycin, pharmaceutically acceptable salts thereof, and derivatives thereof; and spiramycin, pharmaceutically acceptable salts thereof, and derivatives thereof.

The invention additionally relates to a method of treating or preventing a cancer selected from colorectal cancer, Desmoid tumor, bladder cancer, gastric cancer, and breast cancer in a mammal, the method comprising administering to the mammal a therapeutically effective amount of a macrolide antibiotic being one or more of:
tylosin, pharmaceutically acceptable salts thereof, and derivatives thereof;
erythromycin, pharmaceutically acceptable salts thereof, and derivatives thereof; oleandomycin, pharmaceutically acceptable salts thereof, and derivatives thereof; and spiramycin, pharmaceutically acceptable salts thereof, and derivatives thereof;
thereby treating or preventing said cancer.

The invention further relates to a method for treating or preventing, in a mammal, a cancer that expresses a mutated APC gene, the method comprising administering to the mammal a therapeutically effective amount of a macrolide antibiotic being one or more of:
tylosin, pharmaceutically acceptable salts thereof, and derivatives thereof;
erythromycin, pharmaceutically acceptable salts thereof, and derivatives thereof; oleandomycin, pharmaceutically acceptable salts thereof, and derivatives thereof; and spiramycin, pharmaceutically acceptable salts thereof, and derivatives thereof.

Moreover, the invention relates to a Method for treating or preventing cancer in a mammal by suppressing premature stop mutations within the APC gene, the method comprising administering to the mammal a therapeutically effective amount of a macrolide antibiotic being one or more of:
tylosin, pharmaceutically acceptable salts thereof, and derivatives thereof;
erythromycin, pharmaceutically acceptable salts thereof, and derivatives thereof; oleandomycin, pharmaceutically acceptable salts thereof and derivatives thereof; and spiramycin, pharmaceutically acceptable salts thereof, and derivatives thereof;
thereby suppressing premature stop mutations within the APC gene.

BRIEF DESCRIPTION OF THE DRAWINGS

FIG. 4: shows that tylosin treatment suppresses cell tumorigenicity. Five-week-old nude mice were injected with HT-29 CRC cells. Two days post-injection, 0.4 µg/ml tylosin was added to the drinking water of the treated mice group. The water was replaced every 2 days. (A-D) Ten days post-injection the tumor size of the tylosin-treated mice (B, D) is smaller compared to that of the control group (A, C). (E) Mice were sacrificed on day 16. The tumors were excised and weighed. Average tumor masses in grams for control and tylosin-treated mice are shown.

FIG. 5: shows that tylosin treatment changes the histological properties of the tumor. Tumors were removed from control and tylosin-treated mice. The tumors were fixed and stained with Hematoxylin and Eosin (H&E) stain. (A-F) The staining results revealed that the tylosin treatment resulted in necrosis of the tumor without affecting the blood supply (blood vessels are indicated by an arrow). Cross-sections from tumors from three different tylosin-treated mice (D-F) and three different control mice (A-C) are shown.

FIG. 6: Shows that tylosin treatment leads to expression of full-length APC. Tumors were removed from control ("NT") and tylosin-treated (0.8 mg/ml, 0.4 mg/ml) mice. Tumors were lysed and the material probed with anti-APC antibodies. HCT116 cells carry a wild-type APC protein, which serves as a size marker. Tylosin treatment resulted in expression of full-length APC, and a higher amount of tylosin increased the expression of the full-length protein accordingly.

DETAILED DESCRIPTION OF THE INVENTION

Figure 1:
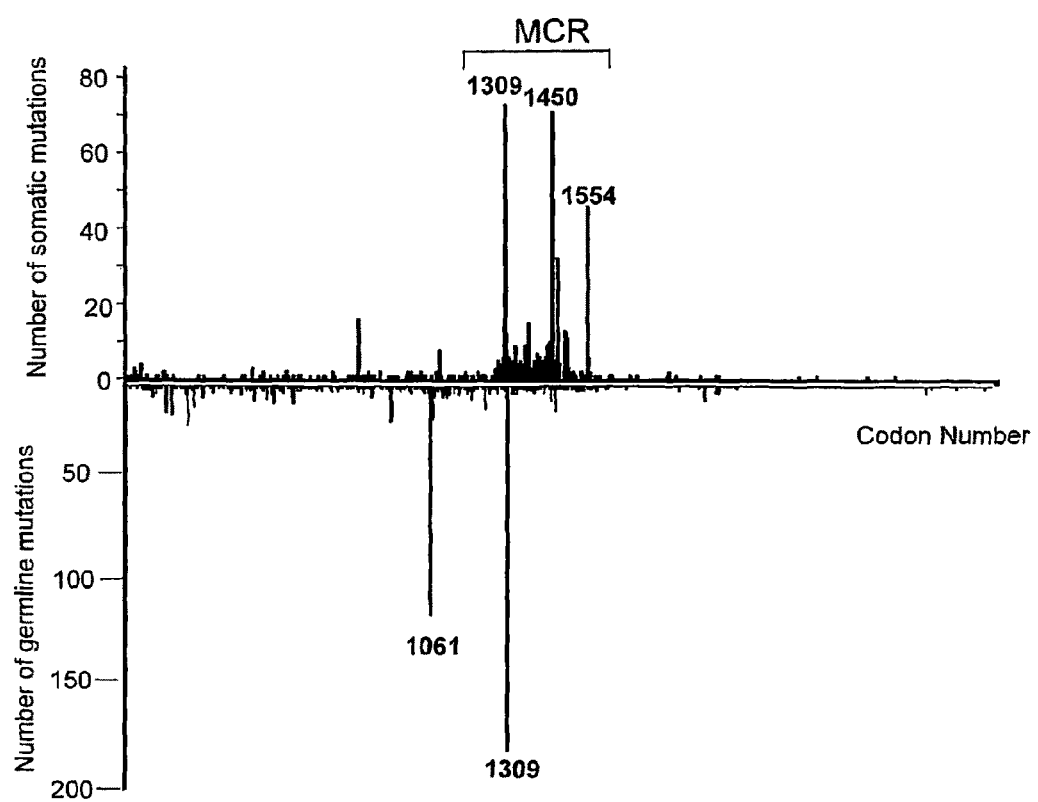
FIG. 1: shows spectrum of somatic and germline mutations in the APC gene. Distribution of somatic (n=829) and germline (n=915) mutations in the APC gene according to codon number. Data derived from: Thierry Soussi (1998), APC gene: database of germline and somatic mutations in human tumors and cell lines. *Nucleic Acids Research* 26(1): 269-270.

The present invention is based on the finding that tylosin, erythromycin, and spiramycin, members of the macrolide family of antibiotics can induce readthrough of the premature stop codon mutations in the APC gene.

The present inventor have now determined that macrolide antibiotics may have clinical uses as compounds that can cause readthrough of the cancer-causing hotspots for premature stop codons in the APC gene.

The present inventor investigated whether macrolides can readthrough the cancer-causing premature stop codon mutations in APC. Evidence is provided herein showing that tylosin, a member of the macrolide family of antibiotics, and additional macrolide compounds (e.g. erythromycin, spiramycin) can induce readthrough of the premature stop codons in the APC gene. The present findings may have clinical applicability in maximizing the effect of stop codon suppressors on APC while minimizing side effects.

The identification of clinically useful methods to suppress premature stop mutations within the APC gene may be of benefit to patients with CRC and other patients suffering from different types of cancers that express a mutated APC. For example, APC mutations have been found in other cancer types, such as Desmoid tumor, bladder cancer, gastric cancer, and breast cancer.

Thus, according to one aspect of the present invention there is provided use of a macrolide antibiotic for the manufacture of a medicament for the treatment or prevention of a cancer selected from colorectal cancer, Desmoid tumor, bladder cancer, gastric cancer, and breast cancer, the macrolide antibiotic being one or more of:
    tylosin, pharmaceutically acceptable salts thereof, and derivatives thereof;
    erythromycin, pharmaceutically acceptable salts thereof, and derivatives thereof; oleandomycin, pharmaceutically acceptable salts thereof, and derivatives thereof; and spiramycin, pharmaceutically acceptable salts thereof, and derivatives thereof.

According to another aspect of the present invention there is provided a pharmaceutical composition for the treatment or prevention of a cancer selected from colorectal cancer, Desmoid tumor, bladder cancer, gastric cancer, and breast cancer, comprising as an active ingredient a therapeutically effective amount of a macrolide antibiotic being one or more of:
    tylosin, pharmaceutically acceptable salts thereof, and derivatives thereof;
    erythromycin, pharmaceutically acceptable salts thereof, and derivatives thereof; oleandomycin, pharmaceutically acceptable salts thereof, and derivatives thereof; and spiramycin, pharmaceutically acceptable salts thereof, and derivatives thereof;
    and a pharmaceutically acceptable carrier.

According to yet another aspect of the present invention there is provided use of a macrolide antibiotic for the manufacture of a medicament for the treatment or prevention of a cancer that expresses a mutated APC gene, the macrolide antibiotic being one or more of:
    tylosin, pharmaceutically acceptable salts thereof, and derivatives thereof;
    erythromycin, pharmaceutically acceptable salts thereof, and derivatives thereof; oleandomycin, pharmaceutically acceptable salts thereof, and derivatives thereof; and spiramycin, pharmaceutically acceptable salts thereof, and derivatives thereof.

According to a preferred embodiment the cancer is selected from colorectal cancer, Desmoid tumor, bladder cancer, gastric cancer, and breast cancer.

Preferably the macrolide antibiotic is tylosin or tylosin tartrate.

According to an additional aspect of the present invention there is provided a method of treating or preventing a cancer selected from colorectal cancer, Desmoid tumor, bladder cancer, gastric cancer, and breast cancer in a mammal, the method comprising administering to the mammal a therapeutically effective amount of a macrolide antibiotic being one or more of:
    tylosin, pharmaceutically acceptable salts thereof, and derivatives thereof;
    erythromycin, pharmaceutically acceptable salts thereof, and derivatives thereof; oleandomycin, pharmaceutically acceptable salts thereof, and derivatives thereof; and spiramycin, pharmaceutically acceptable salts thereof, and derivatives thereof;
    thereby treating or preventing said cancer.

According to yet an additional aspect of the present invention there is provided a method for treating or preventing, in a mammal, a cancer that expresses a mutated APC gene, the method comprising administering to the mammal a therapeutically effective amount of a macrolide antibiotic being one or more of:
    tylosin, pharmaceutically acceptable salts thereof, and derivatives thereof;
    erythromycin, pharmaceutically acceptable salts thereof, and derivatives thereof; oleandomycin, pharmaceutically acceptable salts thereof, and derivatives thereof; and spiramycin, pharmaceutically acceptable salts thereof, and derivatives thereof.

According to a further aspect of the present invention there is provided a method for treating or preventing cancer in a mammal by suppressing premature stop mutations within the APC gene, the method comprising administering to the mammal a therapeutically effective amount of a macrolide antibiotic being one or more of:
    tylosin, pharmaceutically acceptable salts thereof, and derivatives thereof;
    erythromycin, pharmaceutically acceptable salts thereof, and derivatives thereof; oleandomycin, pharmaceutically acceptable salts thereof, and derivatives thereof; and spiramycin, pharmaceutically acceptable salts thereof, and derivatives thereof;
    thereby suppressing premature stop mutations within the APC gene.

According to a preferred embodiment the cancer is selected from colorectal cancer, Desmoid tumor, bladder cancer, gastric cancer, and breast cancer.

Preferably the macrolide antibiotic is tylosin or tylosin tartrate.

The macrolide antibiotic may be a single active agent (i.e. a single macrolide antibiotic) or a combination of two ore more active agents.

As used herein the term "medicament" refers to a pharmaceutical composition. Specifically, it refers to a pharmaceutical composition comprising at least one macrolide antibiotics described in the present invention in any suitable pharmaceutical acceptable carrier (e.g. an excipient or diluent), and also to different formulations required for different routes of administration. For example the medicament may be formulated for oral administration, or may be formulated for parenteral or rectal administration.

The active ingredients of a pharmaceutical composition as disclosed herein may include at least one macrolide antibiotic, i.e. a single active agent (macrolide antibiotic), or two or more active agents.

As used herein, the term "mammal" refers to any member of the class Mammalia, including a human. Preferably, the mammal herein is a human.

As used herein the term "treating" or "treatment" of a disease or a symptom or characteristic of a disease (e.g., colorectal cancer, colorectal adenomas and adenocarcinomas, Desmoid tumor, bladder cancer, gastric cancer, breast cancer, adenomas and adenocarcinomas associated with any one of the types of cancers indicated above) may include any one or more of the following: (1) preventing the disease, i.e. causing the clinical symptoms or signs of the disease not to develop in a mammal that may be exposed to or predisposed to the disease (e.g., a mammal who expresses a mutated APC gene in their somatic or germline cells or who shows a family history of the disease) but which does not yet experience or display symptoms or signs of the disease; (2) inhibiting the disease, i.e., arresting or reducing the rate of development of the disease or its clinical symptoms or signs; (3) relieving the disease, i.e., causing partial or complete regression of the disease or its clinical symptoms or signs; and (4) a combination of (1), (2) or (3) above encompassing different clinical symptoms or signs. As used herein the term "treating" or "treatment" also includes the eradication, removal, modification, or control of primary, regional, or metastatic cancer tissue; and the minimizing or delay of the spread (metastasis) of the cancer (e.g., a colorectal cancer).

As used herein, the term "preventing" or "prevention" includes the prevention of the recurrence, spread or onset of cancer in a patient.

The term "preventing" or "prevention" includes also prevention of adenomas and adenocarcinomas related to any of the above indicated types of cancers.

It is appreciated that treatment or prevention of a cancer according to the invention may involve the mechanism of suppressing premature stop mutations. A premature stop codon results in a truncated (mutant) protein.

As used herein, the term "suppression" or "suppressing", when used in reference to premature stop mutations or premature stop codons, means the process of readthrough of a stop codon which is present in a mutant allele but not present in the wild-type gene (e.g., the APC gene (SEQ. ID. NO:2)).

As used herein, the term "readthrough", when referring to the process of translation, means reading a stop codon ("nonsense" codon) as a "sense" codon (i.e., a codon which codes for an amino acid) or bypassing said stop codon.

As used herein, the term "premature", when referring to a stop codon, means a stop codon which arises as a result of a somatic, germline or sporadic mutation (e.g., a frameshift or a nonsense mutation) in a DNA (mRNA) sequence, but which is not present in the wild-type DNA (mRNA) sequence.

A "therapeutically effective amount" means the amount of a compound (macrolide antibiotic described in the present invention) that, when administered to a mammal to treat a disease (e.g. colorectal cancer, colorectal adenomas or adenocarcinomas), is sufficient to effect partial or total treatment or prevention of the disease. As used herein, a "therapeutically effective amount" also includes that amount of a compound of the invention sufficient to destroy, modify, control or remove a primary, regional or metastatic cancer cell or tissue; delay or minimize the spread of cancer; or provide a therapeutic benefit in the treatment or management of cancer. A "therapeutically effective amount" also includes the amount of a compound of the invention sufficient to result in cancer cell death.

A "therapeutically effective amount" additionally includes the amount of the macrolide antibiotic of the invention sufficient to induce readthrough of the premature stop codons in the APC gene.

A "therapeutically effective amount" additionally includes the amount of a macrolide antibiotic sufficient to suppress premature stop mutations within the APC gene.

The "therapeutically effective amount" may vary depending on the compound, the disease and its status or severity, the age, weight, other medical conditions, etc., of the mammal to be treated. The therapeutically effective amount may also vary depending on one or more past or concurrent medical, surgical, or radiation therapy interventions.

As used herein, the term "pharmaceutically acceptable salts" refers to the reaction product of one or more molecules of any non-toxic, organic or inorganic acid with the compounds of the invention. Illustrative inorganic acids which form suitable salts include hydrochloric, hydrobromic, hydroiodic, sulphuric and phosphoric acid and acid metal salts such as sodium monohydrogen orthophosphate and potassium hydrogen sulfate. Illustrative organic acids which form suitable salts include mono-, di- and tricarboxylic acids. Illustrative of such acids are, for example, acetic acid, glycolic acid, lactic acid, pyruvic acid, malonic acid, succinic acid, glutaric acid, fumaric acid, malic acid, tartaric acid, citric acid, ascorbic acid, maleic acid, hydroxymaleic acid, benzoic acid, hydroxybenzoic acid, phenylacetic acid, cinnamic acid, salicylic acid, methane sulfonic acid, ethanesulfonic, etc.

The term "derivative" as used, e.g., in "tylosin or a derivative thereof", "erythromycin or a derivative thereof", "oleandomycin or a derivative thereof", or "spiramycin or a derivative thereof", refers to a chemically modified compound derived from a parent compound (e.g., tylosin, erythromycin, oleandomycin, spiramycin) that differs from the parent compound by one or more elements, substituents and/or functional groups such that the derivative has the same or similar biological properties/activities as the parent compound such as defined under the terms "treating" or "preventing" (e.g. reducing tumor size and mass, inducing readthrough of the pre-mature stop codons in the APC gene).

Examples of derivatives are prodrugs of the parent compounds for example an ester or amide thereof, which upon administration to a mammal is capable of providing (such as by metabolic process) a compound of the present invention or an active metabolite thereof.

Erythromycin salts and derivatives may include, without limitation, erythromycin lactobionate, erythromycin ethylsuccinate, erythromycin stearate, erythromycin estolate, erythromycin estorate, erythromycin acistrate, erythromycin gluceptate, erythromycin propionate, erythromycin salnacedin, erythromycin A, B, C, D, or E, roxithromycin, clarithromycin, azithromycin, dirithromycin, flurithromycin, as well as derivatives such as those shown in U.S. Pat. Nos. 6,777,543, 6,825,171, and 5,602,106, and WO2002/050093, each of which is incorporated herein by reference in its entirety.

Non-limiting examples of tylosin derivatives are, for example, desmycosin, Tylosin B, or tylosin derivatives such as those described in U.S. Pat. Nos. 5,602,106, 4,092,473, 4,205,163, and 4,268,665, each of which is incorporated herein by reference in its entirety.

Non-limiting examples of oleandomycin salts and derivatives may be, e.g., oleandomycin phosphate (matromycin), oleandomycin 2'-O-phosphate, troleandomycin, and triacetyloleandomycin, and derivatives such as those which are described in U.S. Pat. Nos. 5,602,106, 4,429,116, 4,124,755, and 4,064,143, each of which is incorporated herein by reference in its entirety.

It is appreciated that the macrolide antibiotics "spiramycin" encompass any one of the compounds spiramycin I, II, or III described in The Merck Index, An Encyclopedia of Chemicals, Drugs, and Biologicals, Eleventh Edition, 1989

(paragraph 8708), incorporated herein by reference in its entirety, or any combination thereof (e.g. a combination of spiramycin I, II, and III).

Some non-limiting examples of spiramycin derivatives are, e.g., neospiramycin, dihydrospiramycin, and derivatives such as those which are described in U.S. Pat. Nos. 5,602,106 and 4,174,391, each of which is incorporated herein by reference in its entirety.

It is appreciated that the active ingredients (macrolide antibiotics) described in the present invention also encompass solvates thereof.

As used herein, the term "solvate" refers to a complex of variable stoichiometry formed by a solute (in this invention, a macrolide antibiotic or a salt or derivative thereof) and a solvent. Such solvents for the purpose of the invention may not interfere with the biological activity of the solute. Examples of suitable solvents include, but are not limited to, water, ethanol and acetic acid.

The therapeutically effective amount of the macrolide antibiotics is preferably administered to a mammal in a pharmaceutical composition.

As used herein, a "pharmaceutical composition" refers to a preparation of one or more compounds (macrolide antibiotics) described herein, along with other inert chemical components such as suitable pharmaceutically acceptable carriers. The purpose of a pharmaceutical composition is to facilitate administration of an active ingredient (macrolide antibiotic) to a mammal.

As used herein, the term "pharmaceutically acceptable carrier" refers to an inert non-toxic carrier or diluent that does not cause significant irritation to a subject (mammal) and does not abrogate the biological activity and properties of the administered active ingredient.

Examples, without limitation, of carriers are lactose, sucrose, water, organic solvents and polyethyleneglycol.

The carriers may include additional excipients such as binders, disintegrants, lubricants, surface active agents (surfactants), emulsifiers, preservatives and favoring agents.

Pharmaceutical compositions for use in the context of the present invention include compositions wherein the active ingredient is contained in an amount effective to achieve the intended purpose.

According to a preferred embodiment of the present invention, the route of administration of the composition is selected from oral, parenteral or rectal.

The parenteral route of administration may be for example intravenous, intramuscular, intraperitoneal, intratumoral, and subcutaneous administration.

A specific embodiment is the oral route of administration.

The dosage forms of an active agent (active ingredient) suitable for oral administration include, for example, the forms of solid, semi-solid, liquid, or gas states. Specific examples include tablet, capsule, powder, granule, solution, suspension, syrup, and elixir. However, the forms of agents are not limited to these forms.

The dosage form may be designed to provide immediate release, sustained release or pulsed release of the anticancer active agent (macrolide antibiotic).

Moreover, the anticancer active agent of the present invention may be administered in the form of aerosol or inhalant prepared by charging the active agent in the form of liquid or fine powder, together with a gaseous or liquid spraying agent and, if necessary, a known auxiliary agent such as an inflating agent, into a non-pressurized container such as an aerosol container or a nebulizer. As the spraying agent, a pressurized gas of, for example, dichlorofluoromethane, propane or nitrogen, may be used.

Injections may be prepared by dissolving, suspending or emulsifying the anticancer active ingredient of the invention into an aqueous or non-aqueous solvent such es vegetable oil, glyceride of synthetic resin acid, ester of higher fatty acid, or propylene glycol, by a known method, and if desired, further adding an additive such as a solubilizing agent, an osmoregulating agent, an emulsifier, a stabilizer, or a preservative, which may be used conventionally.

For rectal administration, a suppository may be used. The suppository may be prepared by mixing the anticancer active ingredient of the present invention with an excipient that can be melted at body temperature but is solid at room temperature, such as cacao butter, carbon wax or polyethylene glycol and molding the resultant material, by a known method.

The anticancer active agent may be co-administered with chemotherapy, radiotherapy, or another active agent.

The dose of the anticancer active ingredient of the present invention may be appropriately set or adjusted in accordance with an administration form, an administration route, a degree or stage of a target disease, and the like. For example, for treating colorectal cancer, the general range of effective administration rates of the compounds of the present invention maybe 2-100 mg/kg body weight/day. Preferably a dose may be set at 2-30 mg/kg body weight/day for oral administration of an active ingredient, but the dose is not limited thereto.

For the treatment of the other cancer types, such as Desmoid tumor (aggressive fibromatoses), bladder cancer, gastric cancer, and breast cancer, the dose may be in the range 2-100 mg/kg body weight/day. Preferably a dose may be set at 2-50 mg/kg body weight/day for oral administration of an active ingredient, but the dose is not limited thereto.

The dose administered to a mammal, in particular a human, should be sufficient to prevent cancer, delay its onset, or slow (or stop) its progression. One skilled in the art will recognize that dosage will depend upon a variety of factors including the strength of the particular compound employed, as well as the age, species, condition, and body weight of the mammal. The size of the dose will also be determined by the route, timing, and frequency of administration as well as the existence, nature, and extent of any adverse side-effects that might accompany the administration of a particular compound and the desired physiological effect.

Suitable doses and dosage regimens can be determined by conventional range-finding techniques known to those of ordinary skill in the art. Generally, treatment is initiated with smaller dosages, which are less than the optimum dose of the compound. Thereafter, the dosage is increased by small increments until the optimum effect under the circumstances is reached.

An effective dosage and treatment protocol can be determined by routine and conventional means, starting with a low dose in laboratory animals and then increasing the dosage while monitoring the effects, and systematically varying the dosage regimen as well. Animal studies, preferably mammalian studies, are commonly used to determine the maximal tolerable dose ("MTD") of bioactive agent per kilogram weight. Those skilled in the art regularly extrapolate doses for efficacy, while avoiding toxicity, in other species, including humans.

Thus, in accordance with the above, in therapeutic applications, the dosages of the active agents used in accordance with the invention vary depending on the active agent, the age, weight, and clinical condition of the recipient patient, and the experience and judgment of the clinician or practitioner administering the therapy, among other factors affecting the selected dosage. Generally, the dose should be sufficient to result in slowing, and preferably regressing, the growth of the tumors and most preferably causing complete regression of the cancer. An effective amount of an active ingredient (macrolide antibiotic) is that which provides an objectively identifiable improvement as noted by the clinician or other qualified observer. Regression of a tumor in a patient is typically measured with reference to the diameter of a tumor. Decrease in the diameter of a tumor indicates regression. Regression is also indicated by failure of tumors to reoccur after treatment has stopped.

Dosing may be in one or a combination of two or more administrations, e.g., daily, bi-daily, weekly, monthly, or otherwise in accordance with the judgment of the clinician or practitioner, taking into account factors such as age, weight, severity of the disease, and the dose administered in each administration.

EXAMPLES

Methods and Materials

Culturing of Cells

HCT116 CRC cells (control cells carrying a wild-type APC) were cultured in Dulbecco's modified Eagle's medium (DMEM) supplemented with 10% fetal calf serum (FCS) and 100 units/ml penicillin or streptomycin. Cells were kept in a humidified, 5% $CO_2$ atmosphere at 37° C. Cells were transfected using JetPEI (PolyPlus Transfection). The cells were transfected with 0.5 µg of the described construct, and 48 hours later, the levels of luciferase were measured with the Luciferase assay kit (Promega, USA), according to the manufacturer's instructions.

Cells were maintained as described above. Cells were transfected with 0.5 µg of pTOPFLASH and 0.05 µg Renilla (Promega, USA). Forty-eight hours later, the levels of luciferase were measured by using the Luciferase assay kit (Promega, USA).

In Vivo Mouse Experiments

Six female Nude mice (SCID) were injected with $1 \times 10^7$ HT-29 cells. For fourteen days treated groups were fed a normal mouse diet and received drinking water containing 0.4 mg/ml of tylosin. The control group received regular drinking water. Following fourteen days, the mice were sacrificed and the tumors were removed and weighed.

Tumor sections from control and treated mice were stained with H&E stain. The slides were examined by a professional pathologist.

Tumors from control and treated mice were lysed, run on an SDS-PAGE gel, and transferred to a nitrocellulose membrane. The membrane was incubated with an anti-APC antibody (oncogene APC AB-2).

Spectrum of Somatic and Germline Mutations in the APC Gene.

The sites of most of the known sporadic and hereditary APC mutations are shown below. The most common germline mutations in APC occur at codons 1061 and 1309. Most of the APC somatic mutations are clustered within the MCR (mutation cluster region) with hotspots at codons 1309, 1450 and 1554 (FIG. 1). CRC cell lines with mutations in most of their hotspots are commercially available and were grown in the Lab.

APC Hotspot and Surrounding Sequence

The full-length, wild-type APC protein sequence (SEQ ID NO:1) and full-length, wild-type APC DNA sequence (SEQ ID NO:2) are provided.

The following table illustrates the sequence of the stop codons, as well as the sequences surrounding them at the mutational hotspots of the APC gene. Note that at hotspots 1061, 1450 and 1554, the frameshift or nonsense stop codon formed is TGA, whereas at hotspot 1309, the stop codon is TAG (see Table 1).

TABLE 1

| Mutation site | Wild type sequence | Mutated sequence |
|---|---|---|
| 1061 | GAA ATA AAA CAA AGT GAG CAA (SEQ. ID. NO: 3) | GAA ATA AAG TGA GCA A (SEQ. ID. NO: 4) |
| 1309 | ATA AAA GAA AAG ATT GGA ACT AGG (SEQ. ID. NO: 5) | ATA AAA GAT TGG AAC TAG G (SEQ. ID. NO: 6) |
| 1450 | ACC AAG CGA GAA GTA (SEQ. ID. NO: 7) | ACC AAG TGA GAA GTA (SEQ. ID. NO: 8) |
| 1554 | GAA AAA△ACT ATT GAT (SEQ. ID. No: 9) | GAA AAA AAC TAT TGA T (SEQ. ID. NO: 10) |

The table shows the stop codons and the surrounding sequences generated by the mutations in the hotspots. In mutation sites 1061 and 1309, the rectangles show the site of mutational events resulting in a 5-bp deletion, leading to the formation of a stop codon just downstream from the deletion. At codon 1450, the rectangle shows the site of a missense mutation that results in a stop codon (a nonsense mutation). The triangle just after codon 1554 indicates the site of the insertion of an adenine that leads to the downstream formation of the stop codon. In all cases the bold codon represents the stop codon formed by the nonsense or reading frame mutation.

Example 1

Tylosin-Induced Mutant APC Stop Codon Readthrough

The tylosin used in the following experiments was commercial tylosin tartrate bought from Sigma Chemicals, Israel (Catalogue No. T6134); Spiramycin was bought from Sigma Chemicals, Israel (Catalogue No. S-9132); and Erythromycin was bought from Fluka, Switzerland (Catalogue No. 45673). Oleandomycin can be obtained from Sigma Chemicals, Israel (Catalogue No. T6514).

Figure 2D:
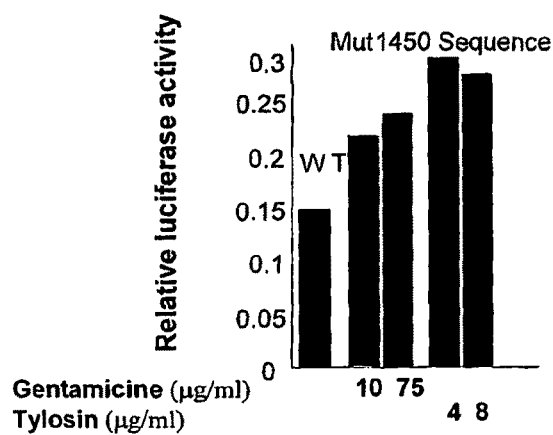
FIG. 2: shows tylosin-induced mutant APC stop codon readthrough. (A) A schema of the reporter plasmid constructed for screening compounds that can readthrough specific APC stop mutations. (B-D) Results obtained using this construct show that tylosin induces higher levels of readthrough compared to erythromycin, spiramycin, and gentamycin at APC hotspots 1061, 1554, and 1450, respectively.

A dual luciferase reporter plasmid system was used to measure the effect of tylosin on readthrough of APC hotspot stop codon mutations in colorectal tissue culture cells. In this system, the Renilla luciferase reporter gene is located upstream of the hotspot, and the firefly luciferase reporter gene is located downstream of the hotspot in the APC wild-type or mutated sequences, and both genes are under the transcriptional control of the APC promoter (FIG. 2a). The Renilla luciferase gene serves as an internal normalization control for transfection efficiency, mRNA abundance and the levels of translation initiation, since translation of both enzymes originates from the same translation initiation signal. Following normalization, the differences in firefly luciferase activities reflect the frequency of stop codon readthrough. Constructs containing either wild-type or the APC mutated sequence at the APC hotspot codons 1061 or 1554 were transfected into HCT116 colorectal cancer cells grown in the presence of varying amounts of antibiotics of the macrolide family. Data shows significant levels of APC stop codon readthrough when the cells were treated with various amounts (4-80 µg/ml) of tylosin (FIGS. 2b, 2c). Spiramycin, erythromycin, and gentamycin (an aminoglycoside antibiotic) induced more moderate levels of stop codon readthrough (FIGS. 2b, 2c, 2d).

Example 2

Tylosin Results in Downregulation of β-Catenin/Tcf Signaling

Figure 3:
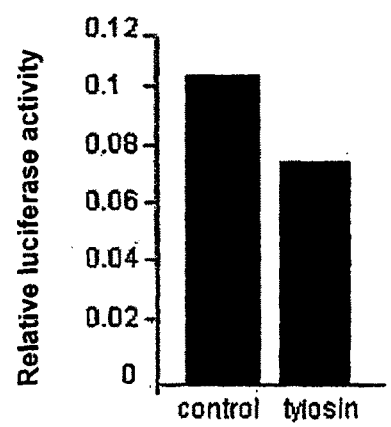
FIG. 3: shows that tylosin downregulates β-catenin/Tcf signaling. Control or tyosin-treated CX-1 cells were transfected with pTOPFLASH. Cells were harvested 48 h after transfection and the luciferase levels were measured.

Colorectal cell lines show high levels of β-catenin/Tcf-mediated transcription due to mutations that lead to overactivation of the Wnt signaling pathway. To measure the effect of tylosin on levels of β-catenin/Tcf-mediated transcription, CX-1 CRC cells containing a stop mutation in APC hotspot 1554 were transfected with pTOPFLASH, a luciferase reporter plasmid that is widely used for measuring transcriptional activity of Tcf and β-catenin (pTOPFLASH contains multimerized Tcf-binding sites linked to a luciferase reporter). The data shows that treatment of CX-1 cells with 8 µg/ml tylosin led to an approximately 50% reduction in β-catenin/Tcf/LEF transcriptional signaling (FIG. 3) A similar result was shown for SW1417 cells, containing an APC hotspot mutation at codon 1450 (results not shown).

Example 3

Tylosin Treatment Suppresses Cell Tumorigenicity

Truncation of APC correlates with tumor formation (15). The present inventor predicted that restoration of functional, full-length APC protein in a cell line containing only truncated APC would lead to a decrease in tumorigenesis. $1 \times 10^7$ HT-29 CRC cells containing a hotspot mutation at codon 1554 of APC were injected into twelve nude SCID mice. The treated mice group (six mice) received 0.4 µg/ml tylosin in the drinking water. The growth of the tumor was monitored and a significant difference was seen in the size of tumors between the control and tylosin-treated mice. The treated mice had reduced tumor size compared with the control mice (FIG. 4a). Following fourteen days of receiving drinking water with or without tylosin, the mice were sacrificed and the tumor was removed. The tumors were weighed and the tumor mass of the tylosin-treated mice was, on average, approximately 40% lower than that of the control group (FIG. 4b).

Example 4

The Tumor Histological Properties Differ Between Control and Tylosin-Treated Mice Tumor sections from control and tylosin-treated mice were stained with Hematoxylin and Eosin (H&E) stain, a stain used routinely for tissue sections, and were examined by a professional pathologist. This staining showed that the tylosin treatment led to necrosis and death of tumor cells (FIG. 5), which may explain the smaller tumor size in the treated mice. The tumor necrosis in the tylosin-treated mice occurred although the blood supply to the tumor was not affected, suggesting that the tylosin can reach the tumor and cause cell death.

Example 5

Effect of Macrolide Antibiotic on Lifespan $1 \times 10^7$ HT-29 CRC cells containing a hotspot mutation at codon 1554 of APC are injected into ten three-week-old nude SCID mice. The treated mice are given 0.3-0.8 µg/ml tylosin, spiramycin, erythromycin, or oleandomycin in the drinking water. Ten control mice receive drinking water without antibiotics. The average lifespans of treated mice are compared with the lifespans of the control mice.

In addition, $Apc^{-/-}$ mice, C57BL/6J-$Apc^{Min}$/J (Jackson Laboratories, Stock No. 002020), which have a stop mutation in APC and spontaneously develop tumors and eventually die, are treated with each of the macrolide antibiotics. The lifespan of treated mice is compared to the lifespans of control, untreated mice.

Example 6

Treatment with Macrolide Salts and Derivatives in a Colon Cancer Model

Female nude SCID mice are injected with $1 \times 10^7$ HT-29 CRC cells containing a hotspot mutation at codon 1554 of APC or with $1 \times 10^7$ SW1417 CRC cells containing a hotspot mutation at codon 1450 of APC. For fourteen days, treated groups are fed a normal mouse diet and drinking water containing 0.4 µg/ml of one of: salts or derivatives of tylosin; salts or derivatives of erythromycin; salts or derivatives of spiramycin; or salts or derivatives of oleandomycin. A control group, also injected with $1 \times 10^7$ HT-29 or SW1414 CRC cells, is given drinking water without a derivative or salt of a macrolide antibiotic and fed the same diet. All mice are sacrificed and the tumor is removed and weighed. Tumor sections from ten control mice as well as from ten mice in each group treated with each of the salts or derivatives of tylosin, erythromycin, spiramycin or oleandomycin, are stained with H&E stain, and are examined by a professional pathologist. The pathologist examines each tumor section for tumor necrosis. The dosage is varied according to the compound tested and the desired effect to be achieved.

In addition, a similar experiment to the above is conducted (without provision of cancer-causing cells) on C57BL/6J-$Apc^{Min}$/J mice, with (treated) and without (control) each of the macrolide antibiotics.

Discussion:

Colon cancer is one of the leading causes of cancer deaths in the Western world. The progression of colon cancer has been closely correlated with molecular changes providing potential targets for therapeutic and diagnostic agents. A unique feature of colon cancer is that mutations in a single gene are found in most tumors. Truncation mutations in the gene encoding for the Adenomatous Polyposis Coli (APC) protein are found in >80% of sporadic colonic tumors and are also responsible for Familial Adenomatous Polyposis (FAP), an inherited form of colon cancer. Loss of APC protein function is an extremely early event in the development of most sporadic colonic tumors and precedes the formation of polyps, which are the precursors to adenoma.

This suggests that the APC protein is essential for the maintenance of intestinal and colonic epithelia, and its expression may provide an appropriate target for intervention.

The APC gene encodes a large multidomain protein that plays an integral role in the Wnt-signalling pathway and in intercellular adhesion. The majority (95%) of the truncating germline mutations are nonsense or frameshift mutations that result in a truncated protein product with abnormal function. The most common germline mutations occur at codons 1061 and 1309, which between them account for a third of all germline mutations (FIG. 1).

Mutations at hotspots 1061 and 1309 are found as both the frameshift and nonsense type. Thus, one allele may contain a frameshift mutation at codon 1061 or 1309, and the allele may be a nonsense (premature stop) mutation at codon 1061 or 1309 (16, 17). Similarly, mutations at hotspot 1554 may be of either frameshift or nonsense type. However, thus far only nonsense mutations have been identified at codon 1450.

Somatic mutations are found in the majority of colorectal adenomas and carcinomas, including adenomas<5 mm in size. Over 60% of all somatic mutations in APC occur within <10% of the coding sequence of the gene, located between codons 1286 and 1513; this region is termed the mutation cluster region (MCR). Within the MCR, there are three hotspots for somatic mutations at codons 1309, 1450 and 1554 (FIG. 1). It is most likely that the role of APC in Wnt-signaling is responsible for its role in colorectal carcinogenesis. Mutant APC may also disrupt intercellular adhesion and stability of the cytoskeleton, both of which play a part in cancer progression. Another APC mutation, at codon 1307, has been found in some persons with colorectal and breast cancers, as well as a few individuals with melanomas, skin cancers, and bladder cancers (14).

As in colorectal cancer, a large number of other human genetic diseases (e.g., cystic fibrosis (CF), Duchenne muscular dystrophy (DMD) (8)) result from mutations that cause the premature termination of the synthesis of the protein encoded by the mutant gene and one way of treating these diseases would be to supplement the cells with a wild-type copy.

For some years it has been known that aminoglycoside antibiotics can suppress disease-associated premature stop mutations by allowing an amino acid to be incorporated in place of a nonsense stop codon, thus permitting translation to continue to the normal end of the transcript. The susceptibility to stop codon suppression depends on the type of stop codons and on the local sequence context surrounding the stop codon. UGA and UAG show higher translation readthrough as compared to UAA. The sequence of the stop codon, as well as the sequence surrounding it in the mutational hotspots of the APC gene, has been illustrated. As can be seen from Table 1, the type of premature stop codons formed at the listed APC hotspots are TGA or TAG.

The utility of this approach was previously demonstrated with the autosomal recessive disease cystic fibrosis (CF) and in a subset of Duchenne (DMD) patients with a nonsense mutation. In both CF and DMD patients, only 5 to 10% of all cases are due to nonsense mutations in the coding sequence. In comparison, in patients with colorectal tumors, premature stop codons in the APC gene are found in around 85% of all cases. Although exact numbers have not been determined, fewer than 80% of the colorectal cancer cases have only nonsense mutations, whereas in other cases, an individual may have one allele with a frameshift mutation and the other with a nonsense mutation.

Studies aimed at restoring the full-length APC protein into cells that lack a functional APC protein have not been conducted so far. However, aminoglycosides such as gentamicin have serious dose-limiting toxicities and currently must be administered intravenously, thus making them an unattractive long-term treatment for these type of disorders. The present inventor screened for other compounds that can readthrough the cancer-causing stop codons in the APC gene and lead to the expression of a functional full-length APC protein in colorectal cancer cells that contain a non-functional truncated APC protein product.

To screen for compounds that can readthrough premature APC stop mutations, the present inventor constructed a reporter assay system that can efficiently and quickly measure the effect of different compounds on levels of readthrough of specific premature APC stop codons. The results indicate that tylosin, a member of the macrolides family of antibiotics that has previously been shown only to readthrough prokaryotic stop codons, can readthrough specific APC hotspot mutations.

Since Wnt signaling levels are a marker for the tumorigenic properties of CRC cells, the present inventor first examined whether tylosin can reduce the high levels of Wnt signaling seen in CRC cells. The results show that tylosin treatment did reduce the levels of Tcf/β-catenin-dependent transcription in the CRC cells tested.

In the next step, the inventor investigated whether tylosin can reduce tumor development in vivo. To this end, HT-29 CRC cells containing an APC hotspot mutation (codon 1554) were injected into nude mice. The treated mouse group received tylosin in the drinking water. The data shows that the tylosin treatment resulted in a reduction of the tumor size and mass compared to the control group. Moreover, the tylosin treatment resulted in enhanced death of the tumor cells without affecting the microvessels.

Readthrough of premature stop codons is potentially an alternative treatment strategy for patients in the early stages of colorectal cancer or who have the genetic background for developing this type of cancer. Taken together, the present results demonstrate that tylosin and other macrolides antibiotics may effect readthrough of the disease-causing premature stop codons in the APC gene that is mutated in the vast majority of colorectal cancer patients. This novel approach may open new avenues in the clinical treatment of colorectal cancer and other genetic human diseases that arise from premature stop codons in important coding sequences.

Example 7

Treatment with Macrolide Antibiotics and their Salts and Derivatives in a Breast Cancer, Bladder Cancer, Gastric Cancer, and Desmoid Tumor Model Female nude SCID mice are injected with cells known to cause breast cancer in a mouse model and containing a mutation at a hotspot mutation of APC. For fourteen days, treated groups are fed a normal mouse diet as well as drinking water containing 0.3-0.8 µg/ml of one of: tylosin or salts or derivatives of tylosin; erythromycin or salts or derivatives of erythromycin; spiramycin or salts or derivatives of spiramycin; or oleandomycin or salts or derivatives of oleandomycin. A control group, also injected with the same breast cancer cells, is given drinking water without a macroloide antibiotic or derivative or salt of a macrolide antibiotic, and fed the same diet. All mice are sacrificed and the tumor is removed and weighed. Tumor sections from control mice as well as from mice treated with each of tylosin, erythromycin, spiramycin or oleandomycin or the salts or derivatives of the macrolide antibiotics, are stained with H&E stain, and are examined by a professional pathologist. The pathologist examines each tumor section for tumor necrosis.

The above methods with respect to breast cancer are repeated for determining the effects of the tested active agents with respect to bladder cancer, gastric cancer, and Desmoid tumor, except that the appropriate cells inducing the mouse model of the respective cancer are injected into treated and control mice.

Example 8

Effect of Macrolide Antibiotics on Cell Tumorigenicity in Utero

Ten pregnant APC$^{-/-}$ mice carrying fetuses are given 0.3-0.8 µg/ml tylosin, spiramycin, erythromycin, or oleandomycin in the drinking water. Ten pregnant control mice receive drinking water without antibiotics. Following birth, the young (baby) mice of the treated groups continue to receive the same macrolide antibiotics in the drinking water, with the control young mice receiving drinking water without antibiotics. Eight weeks after their birth, the young mice are sacrificed, and tumors are removed from their gastrointestinal tracts and weighed. The tumor mass of the control group of young mice is compared with the tumor mass of the tylosin-, spiramycin-, erythromycin-, or oleandomycin-treated groups of young mice (exposed to the macrolides both in utero and after birth).

Example 9

Tumor Histological Properties Differ Between Control and Macrolide Antibiotic-Treated Mice Tumor sections from control and macrolide antibiotic-treated mice in the above experiments are stained with Hematoxylin and Eosin (H&E) stain, a stain used routinely for tissue sections, and is examined by a professional pathologist. Staining is examined to determine whether the macrolide treatment leads to necrosis and death of tumor cells.

REFERENCED PRIOR ART

The following is a list of prior art, which is considered to be pertinent for describing the state of the art in the field of the invention. Acknowledgement of these references herein will be made by indicating the number from their list below within parentheses.

1. Bedwell, D. M. et al. (1997). Suppression of a CFTR premature stop mutation in a bronchial epithelial cell line. Nat. Med. 3:1280-1284.
2. Wilschanski, M., Yahav, Y., Yaacov, Y., Blau, H., Bentur, L., Rivlin, J., Aviram, M., Bdolah-Abram, T., Bebok, Z., Shushi, L., Kerem, B., and Kerem, E. (2003). Gentamicin-induced correction of CFTR function in patients with cystic fibrosis and CFTR stop mutations. N. Engl. J. Med. 15: 1433-1441.
3. Barton-Davis, E. R., Cordier, L., Shoturma, D. I., Leland, S. E. and Sweeney, H. L. (1999). Aminoglycoside antibiotics restore dystrophin function to skeletal muscles of mdx mice. J. Clin. Invest. 104: 375-38.
4. Politano, L., Nigro, G., Nigro, V., Piluso, G., Papparella, S., Paciello, O., and Comi, L. I. (2003). Gentamicin administration in Duchenne patients with premature stop codon: Preliminary results. Acta Myol. 1: 15-21.
5. Kerem, E. (2004). Pharmacologic therapy for stop mutations: how much CFTR activity is enough? Curr. Opin. Pulm. Med. 6:547-52.
6. Laurent-Puig, P., Beroud, C., and Soussi, T (1998). APC gene: database of germline and somatic mutations in human tumors and cell lines. Nucleic Acids Research, 26: 269-270.
7. Thompson, J., Pratt, c.a., and Dahlberg, A. E. (2004). Effects of a number of classes of 50S inhibitors on stop codon readthrough during protein synthesis. Antimicrob. Agents Chemother 12: 4889-4891.
8. Atkinson, J and Martin, R. (1994). Mutations to nonsense codons in human genetic disease: implications for gene therapy by nonsense suppressor tRNAs. Nucleic Acids Res. 8: 1327-1334.
9. U.S. Pat. No. 5,324,720
10. US Patent Application Publication No. 2005/0171032
11. Alman, B. A., Li, C. Pajerski, M. E., Diaz-Cano, S. and Wolfe, H. J. (1997). Increased beta-catenin protein and somatic APC mutations in sporadic aggressive fibromatoses (desmoid tumors). Am. J. Pathol. 151: 329-334.
12. Bohm, M., Kirch, H., Otto, T., Rubben, H. and Wieland, I. (1997). Deletion analysis at the DEL-27, APC and MTS1 loci in bladder cancer: LOH at the DEL-27 locus on 5p13-12 is a prognostic marker of tumor progression. Int. J. Cancer 74: 291-295.
13. Oh, S. T., Yoo, N. J. and Lee, J. Y. (1999). Frequent somatic mutations of the beta-catenin gene in intestinal-type gastric cancer. Cancer Res. 59: 4257-4260.
14. Wills, J. C. et al. (2002). "Hot spots" can burn you, Am. J. Gastroenterology 97(3): 757-758.
15. Fearnhead et al. (2001). The ABC of APC. Hum. Mol. Genet. 10:721-723.
16. Crabtree et al. (2003). Oncogene 22: 4257-4265.
17. Albuquerque et al. (2002). Hum. Mol. Genet. 11: 1549-1560.

All publications, patents and patent applications mentioned in this specification are herein incorporated in their entirety by reference into the specification, to the same extent as if each individual publication, patent or patent application was specifically and individually indicated to be incorporated herein by reference.

What is claimed is:

1. A method for treating a human subject having colorectal cancer that expresses a mutated APC gene that contains a premature stop codon caused by a nonsense mutation, comprising treating the human subject by administering to the human subject, as active agent, a therapeutically effective amount of tylosin or erythromycin, or a pharmaceutically acceptable salt or prodrug of tylosin or erythromycin, wherein said treating excludes preventing the colorectal cancer.

2. The method of claim 1, wherein said active agent is tylosin or a pharmaceutically acceptable salt or prodrug thereof.

3. The method of claim 1, wherein said active agent is erythromycin, or a pharmaceutically acceptable salt or prodrug thereof.

4. A method for identifying and treating a human subject that has a mutated APC gene containing a premature stop codon mutation caused by a nonsense mutation, the subject having early stage colorectal cancer, comprising:
   identifying a human subject who has said mutated APC gene and that has early stage colorectal cancer: and
   treating the human subject identified in said identifying step by administering to the human subject a therapeutically effective amount of tylosin or erythromycin, or a pharmaceutically acceptable salt or prodrug of tylosin or erythromycin, wherein said treating excludes preventing the colorectal cancer.

5. The method of claim 4, wherein the human subject is administered tylosin or a pharmaceutically acceptable salt or prodrug thereof.

6. The method of claim 4, wherein the active agent is erythromycin, or a pharmaceutically acceptable salt or prodrug thereof.

7. The method of claim 4, wherein the human subject also has Familial Adenomatous Polyposis (FAP).

8. The method of claim 5, wherein the human subject has Familial Adenomatous Polyposis (FAP).

9. The method of claim 1, wherein said active agent is erythromycin lactobionate, erythromycin stearate, erythromycin gluceptate, erythromycin salnacedin, erythromycin A, erythromycin C, erythromycin E, roxithromycin, clarithromycin, azithromycin, and flurithromycin.

10. The method of claim 4, wherein said active agent is erythromycin lactobionate, erythromycin stearate, erythromycin gluceptate, erythromycin salnacedin, erythromycin A, erythromycin C, erythromycin E, roxithromycin, clarithromycin, azithromycin, and flurithromycin.

11. A method for identifying and treating a human subject that has a mutated APC gene containing a premature stop codon mutation caused by a nonsense mutation, the subject having a genetic predisposition to the development of colorectal cancer, comprising:
   identifying a human subject who has said mutated APC gene and that has a genetic predisposition to the development of colorectal cancer; and
   treating the human subject identified in said identifying step by administering to the human subject a therapeutically effective amount of tylosin or erythromycin, or a pharmaceutically acceptable salt or prodrug of tylosin or erythromycin.

12. The method of claim 11, wherein said active agent is tylosin or a pharmaceutically acceptable salt or prodrug thereof.

13. The method of claim 11, wherein the active agent is erythromycin, or a pharmaceutically acceptable salt or prodrug thereof.

14. The method of claim 11, wherein said active agent is erythromycin lactobionate, erythromycin stearate, erythromycin gluceptate, erythromycin salnacedin, erythromycin A, erythromycin C, erythromycin E, roxithromycin, clarithromycin, azithromycin, and flurithromycin.

* * * * *